United States Patent [19]
Kosaka et al.

[11] Patent Number: 5,462,694
[45] Date of Patent: Oct. 31, 1995

[54] MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

[75] Inventors: Yoko Kosaka, Atsugi; Takao Takiguchi, Tokyo; Takashi Iwaki, Machida; Takeshi Togano, Yokohama; Shinichi Nakamura, Isehara; Ikuo Nakazawa, Atsugi, all of Japan

[73] Assignee: Canon Kabushiki Kaisha, Tokyo, Japan

[21] Appl. No.: 297,777

[22] Filed: Aug. 30, 1994

[30] Foreign Application Priority Data

Aug. 31, 1993 [JP] Japan .................................. 5-237213
Aug. 26, 1994 [JP] Japan .................................. 6-224046

[51] Int. Cl.$^6$ ............. C09K 19/34; C09K 19/32; C09K 19/30; G02F 1/13
[52] U.S. Cl. .............. 252/299.61; 252/299.62; 252/299.63; 359/103; 548/122; 548/125; 548/217; 548/218; 549/283; 549/369; 549/429; 549/295; 544/146; 544/128; 544/353; 544/298; 534/659; 585/27
[58] Field of Search .................. 252/299.61, 299.62; 548/122, 125, 217, 218, 219, 220, 136; 544/146, 128, 353, 298; 549/283, 429, 448, 263, 273, 295, 369; 534/659; 585/27

[56] References Cited

U.S. PATENT DOCUMENTS

| | | | |
|---|---|---|---|
| 4,367,924 | 1/1983 | Clark et al. | 359/53 X |
| 4,834,905 | 5/1989 | Eidenschenk | 252/299.61 |
| 5,002,694 | 3/1991 | Wachtler et al. | 252/299.61 |
| 5,075,030 | 12/1991 | Togano et al. | 252/299.61 |
| 5,091,109 | 2/1992 | Takiguchi et al. | 252/299.61 |
| 5,118,441 | 6/1992 | Mori et al. | 252/299.61 |
| 5,176,845 | 1/1993 | Yamada et al. | 252/299.61 |
| 5,190,690 | 3/1993 | Takiguchi et al. | 252/299.61 |
| 5,284,599 | 2/1994 | Iwaki et al. | 252/299.61 |
| 5,318,720 | 6/1994 | Takiguichi et al. | 252/299.61 |
| 5,354,501 | 10/1994 | Nakamura et al. | 252/299.62 |
| 5,360,577 | 11/1994 | Buchecker et al. | 252/299.61 |
| 5,384,070 | 1/1995 | Hemmerling et al. | 252/299.61 |
| 5,385,692 | 1/1995 | Iwaki et al. | 252/299.62 |

FOREIGN PATENT DOCUMENTS

| | | |
|---|---|---|
| 0344557 | 12/1989 | European Pat. Off. . |
| 0541081 | 5/1993 | European Pat. Off. . |
| 0546338 | 6/1993 | European Pat. Off. . |
| 0552658 | 7/1993 | European Pat. Off. . |
| 56-107216 | 8/1981 | Japan . |
| 4258684 | 9/1992 | Japan . |
| 4264192 | 9/1992 | Japan . |
| WO08019 | 10/1988 | WIPO . |

OTHER PUBLICATIONS

M. Schadt and W. Helfrich, Voltage–Dependent Optical Activity of a Twisted Nematic Liquid Crystal, Feb. 15, 1971, pp. 127–128, Applied Physics Letters, vol. 18, No. 4, Feb. 1971.

Mol. Cryst. & Liq. Cryst., vol. 204 (Jul., 1991) 27–35.

Tetrahedron, vol. 32, (1976) 1835–1838.

*Primary Examiner*—Cynthia Harris
*Attorney, Agent, or Firm*—Fitzpatrick, Cella, Harper & Scinto

[57] ABSTRACT

A mesomorphic compound of the formula (I) according to claim 1 characterized by having at least one cyclic group selected from β class including, e.g., thiazole-2,5-diyl, benzoxazole-2,5-diyl, indan-2,5-diyl, and quinoxaline-2,6-diyl and also having a linkage of $Y^1-(CH_2)_m-Y^2$, where $Y^1$ and $Y^2$ are —$CH_2$—, —O—, —COO— or —OCO— and m is 1–16, is suitable as a component for a liquid crystal composition providing improved response characteristics. A liquid crystal device is constituted by disposing the liquid crystal composition between a pair of substrates. The liquid crystal device is used as a display panel constituting a liquid crystal apparatus providing good display characteristics.

25 Claims, 4 Drawing Sheets

MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

FIELD OF THE INVENTION AND RELATED ART

The present invention relates to a mesomorphic compound, a liquid crystal composition, a liquid crystal device, a display apparatus and a display method, and more particularly to a mesomorphic compound, a liquid crystal composition containing the compound with improved responsiveness to an electric field, a liquid crystal device using the composition for use in a display device, a liquid crystal-optical shutter, etc., a liquid crystal apparatus using the device particularly as a display device, and a display method of using the composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. have been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, high contrast, etc.

More specifically, among a response time τ, the magnitude of spontaneous polarization Ps and viscosity η, the following relationship (II) exists: $\tau = \eta/(Ps \cdot E)$ ... (II), where E is an applied voltage. Accordingly, a high response speed can be obtained by (a) increasing the spontaneous polarization Ps, (b) lowering the viscosity η, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

In general, in a liquid crystal device utilizing birefringence of a liquid crystal, the transmittance under right angle cross nicols is given by the following equation:

$$I/I_0 = \sin^2 4\theta \cdot \sin^2(\Delta nd/\lambda)\pi,$$

wherein $I_0$: incident light intensity,

I: transmitted light intensity,

θ: tilt angle,

Δn: refractive index anisotropy, d: thickness of the liquid crystal layer,

λ: wavelength of the incident light.

Tilt angle θ in a ferroelectric liquid crystal with non-helical structure is recognized as a half of an angle between the average molecular axis directions of liquid crystal molecules in a twisted alignment in a first orientation state and a second orientation state. According to the above equation, it is shown that a tilt angle θ of 22.5 degrees provides a maximum transmittance and the tilt angle θ in a non-helical structure for realizing bistability should desirably be as close as possible to 22.5 degrees in order to provide a high transmittance and a high contrast.

However, when a birefringence of a liquid crystal is utilized in a liquid crystal device using a ferroelectric liquid crystal in a non-helical structure exhibiting bistability reported by Clark and Lagerwall, the following problems are encountered, thus leading to a decrease in contrast.

First, a tile angle θ in a ferroelectric liquid crystal with a non-helical structure obtained by alignment with a polyimide film treated by rubbing of the prior art has become smaller as compared with a tilt angle Ⓗ (the angle Ⓗ is a half of the apex angle of the cone as shown in FIG. 2) in the ferroelectric liquid crystal having a helical structure, thus resulting in a lower transmittance.

Secondly, even if the device provides a high contrast in a static state, i.e., under no electric field application, liquid crystal molecules fluctuate due to a slight electric field at a non-selection period of time in a matrix drive scheme in the case of applying a voltage to the liquid crystal molecules for providing a display image, thus resulting in the display image including a light (or pale) black display state, i.e., a decrease in a contrast.

Thus, as described hereinabove, commercialization of a ferroelectric liquid crystal device requires a liquid crystal composition assuming a chiral smectic phase which provides a high contrast, a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a mesomorphic compound providing a high speed responsiveness, a high contrast and a decreased temperature-dependence of response speed; a liquid crystal composition, particularly a chiral smectic liquid crystal composition containing the mesomorphic compound for providing a practical ferroelectric liquid crystal device as described above; a liquid crystal device including the liquid crystal composition and affording good display performances; a liquid crystal apparatus including the device; and a display method using the composition.

According to the present invention, there is provided a mesomorphic compound represented by the following formula (I):

(I), wherein $R^1$ and $R^2$ independently denote $R^3$ or $R^4$—$A^0$—$Y^1$—$(CH_2)_m Y^2$—, and at least one of $R^1$ and $R^2$ is $R^4$—$A^0$—$Y^1$—$(CH_2)_m Y^2$—, in which $R^3$ denotes H, F, or a linear, branched or cyclized alkyl group having 1–18 carbon atoms capable of including at least one —$CH_2$— group which can be replaced with —O—, —S—, —CO—, —CH=CH—, —C≡C— or —CH(CN)— provided that heteroatoms are not adjacent to each other and capable of including at least one H which can be replaced with F, $R^4$ denotes H, F or a linear or branched alkyl group having 1–12 carbon atoms capable of including at least one —$CH_2$— group which can be replaced with —O—, —S—, —CO—, —CH=CH—, —C≡C— or —CH(CN)— provided that heteroatoms are not adjacent to each other and capable of including at least one H which can be replaced with F, $Y^1$ and $Y^2$ independently denote —$CH_2$—, —O—, —COO— or —OCO—, and m is an integer of 1–16; and A denotes —$A^1$—Z—$A^2$— or —$A^1$—$A^2$—Z—$A^3$— in which Z denotes a single bond, —$CH_2O$—, —$OCH_2$—, —COO—, —OCO—, —COS—, —SCO—, —C≡C— or —CH=CH—, and $A^0$, $A^1$, $A^2$ and $A^3$ independently denote a divalent cyclic group selected from α class or β class listed below, and at least one of $A^0$, $A^1$, $A^2$ and $A^3$ independently denotes a divalent cyclic group selected from the β class, α class: 1,4-phenylene capable of including at least one H which can be replaced with F, $CH_3$ or $CF_3$; 1,4-cyclohexylene; pyrimidine-2,5-diyl; pyridine-2,5-diyl; thiazole-2,5-diyl; thiophene-2,5-diyl; and 2,6-naphthylene, and β class: thiazole-2,5-diyl; benzothiazole-2,6-diyl; benzoxazole-2,5-diyl; indan-2,5-diyl; coumaran-2,5-diyl; quinoxaline-2,6-diyl; quinoline-2,6-diyl; 1,2-dithiolan-3,5-diyl; and furan-2,5-diyl.

According to the present invention, there is further provided a liquid crystal composition containing at least one species of the above-mentioned mesomorphic compound.

The present invention provides a liquid crystal device comprising a pair of electrode plates and the liquid crystal composition described above disposed between the electrode plates.

The present invention further provides a liquid crystal apparatus including the liquid crystal device, particularly including a display panel comprising the liquid crystal device.

The present invention still further provides a display method using the liquid crystal composition described above and controlling the alignment direction of liquid crystal molecules to effect display.

We have found that a mesomorphic quinoxaline compound, represented by the formula (I) provides a wider temperature range showing a mesomorphic phase, a good compatibility with another compound and a low viscosity, and thus is suitable as a component of a liquid crystal composition, particularly a ferroelectric liquid crystal composition and a liquid crystal device including the liquid crystal composition which provide good display characteristics based on improvements in various characteristics such as an alignment characteristic, switching characteristic, responsiveness, a temperature-dependence of response speed, and a contrast. As the mesomorphic compound of the formula (I) according to the present invention has a good compatibility with another (mesomorphic or optically active) compound used herein, it is possible to use the mesomorphic compound of the formula (I) for controlling various properties such as spontaneous polarization, SmC* pitch, Ch pitch, a temperature range showing a mesomorphic phase, optical anisotropy, a tilt angle and dielectric anisotropy, with respect to a liquid crystal mixture or composition.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
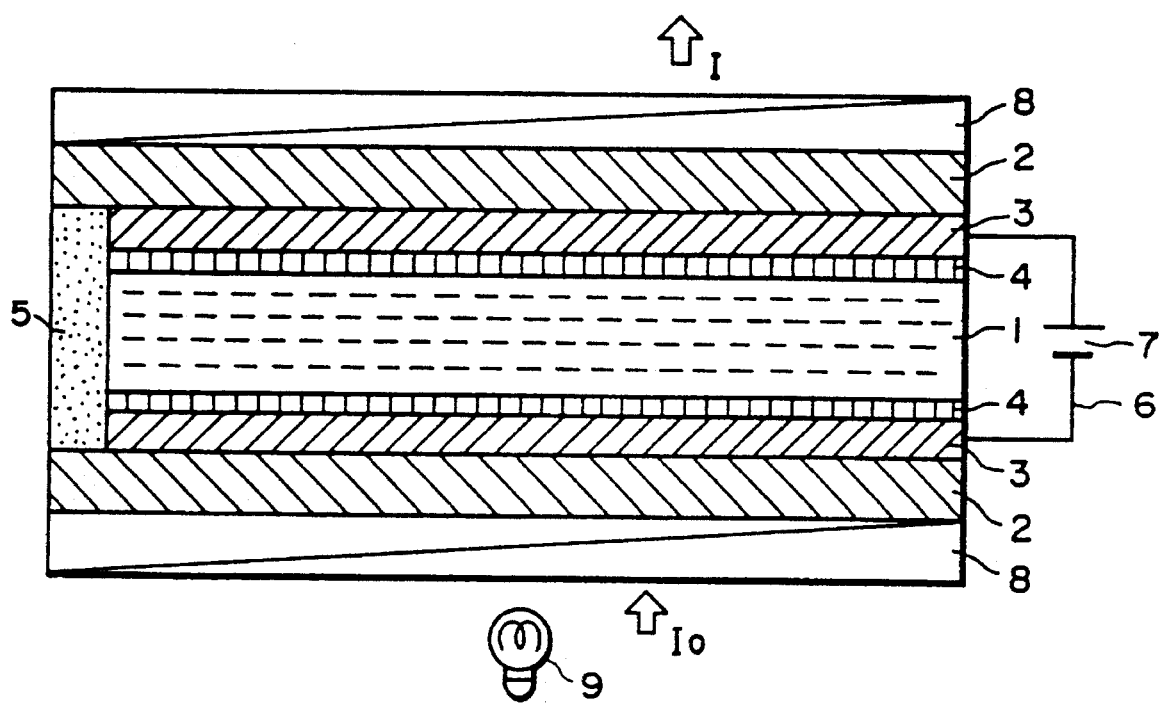
FIG. 1 is a schematic sectional view of a liquid crystal device using a liquid crystal composition assuming a chiral smectic phase.

The mesomorphic compound of the formula (I) according to the present invention is principally characterized by a specific linkage of $-Y^1-(CH_2)_m-Y^2-$ between cyclic groups including at least one cyclic group selected from β class.

Preferred examples of the mesomorphic compound of the formula (I) may include those represented by the following formulae (Ia) to (Ig):

$$R^1-A-(CH_2)_{\overline{m+2}}-A^0-R^4, \quad (Ia)$$

-continued
$$R^1-A-O-(CH_2)_{\overline{m+1}}-A^0-R^4, \quad (Ib)$$

$$R^1-A-OCO-(CH_2)_{\overline{m+1}}-A^0-R^4, \quad (Ic)$$

$$R^1-A-COO-(CH_2)_{\overline{m+1}}-A^0-R^4, \quad (Id)$$

$$R^1-A-(CH_2)_{\overline{m+1}}-O-A^0-R^4, \quad (Ie)$$

$$R^1-A-(CH_2)_{\overline{m+1}}-OCO-A^0-R^4, \text{ and} \quad (If)$$

$$R^1-A-(CH_2)_{\overline{m+1}}-COO-A^0-R^4, \quad (Ig)$$

wherein $R^1$, A, m, $A^0$ and $R^4$ have the meanings as defined above.

The mesomorphic compound of the formula (I) may preferably contain cyclic groups $A^0$, $A^1$ and $A^2$ satisfying the following combinations (a) to (c) or cyclic groups $A^0$, $A^1$, $A^2$ and $A^3$ satisfying the following combination (d):

(a) $A^0$: 1,4-phenylene which is unsubstituted or substituted by at least one F, 1,4-cyclohexylene, or thiophene-2,5-diyl;
$A^1$: benzothiazole-2,6-diyl, benzoxazole-2,5-diyl, thiazole-2,5-diyl, quinoline-2,6-diyl, or quinoxaline-2,6-diyl; and
$A^2$: 1,4-phenylene which is unsubstituted or substituted by at least one F;

(b) $A^0$: 1,4-phenylene which is unsubstituted or substituted by at least one F, 1,4-cyclohexylene, or thiophene-2,5-diyl;
$A^1$: indan-2,5-diyl or coumaran-2,5-diyl; and
$A^2$: pyrimidine-2,5-diyl;

(c) $A^0$: 1,2-dithiolan-3,5-diyl;
$A^1$: pyrimidine-2,5-diyl or pyridine-2,5-diyl; and
$A^2$: 1,4-phenylene which is unsubstituted or substituted by at least one F; and (d) $A^0$: 1,4-phenylene which is unsubstituted or substituted by at least one F, 1,4-cyclohexylene, or thiophene-2,5-diyl;
$A^1$: 1,4-phenylene which is unsubstituted or substituted by at least one F;
$A^2$: thiazole-2,5-diyl; and
$A^3$: 1,4-phenylene which is unsubstituted or substituted by at least one F.

In order to decrease a viscosity, Z between the cyclic groups $A^1$ and $A^2$ or $A^2$ and $A^3$ in the formula (I) may preferably be a single bond.

$R^4$ in $R^4-A^0Y^1-(CH_2)_m Y^2-$ constituting $R^1$ and/or $R^2$ may preferably be any one of the following groups (i) to (iv):

(i) $n-C_aH_{2a+1}-Y^3-$,
(ii) $C_hF_{2h+1}-(CH_2)_i-Y^3-$,
(iii) $F-$, and
(iv) $H-$, wherein a is an integer of 1–12; i is an integer of 0–7; h is an integer of 1–9; and $Y^3$ is a single bond, $-O-$, $-OCO-$ or $-COO-$. Among the above groups, $R^4$ may more preferably be the groups (iii) or (iv), particularly be the group (iv) (i.e., terminal cyclic structure).

At least one $Y^1$ and $Y^2$ in $R^4-A^0-Y^1-(CH_2)_m Y^2-$ may preferably be $-CH_2-$ in view of enlargement of a temperature range showing a mesomorphic (liquid crystal) phase. Further, when $A^0$ is a cyclic group selected from α group, particularly 1,4-phenylene and 1,4-cyclohexylene, $Y^1$ and/or $Y^2$ may preferably be $-CH_2-$ in view of a decrease in viscosity.

m in $R^4-A^0-Y^1-(CH_2)_m-Y^2-$ may preferably be 1–10, more preferably be 2–6.

When $R^4-A^0-Y^1-(CH_2)_m-Y^2-$ is the above-mentioned preferred examples thereof, the cyclic groups $A^0$, $A^1$ $A^2$ and $A^3$ may preferably be any one of the above-mentioned combinations (a) to (d). In such a case, the mesomorphic compound of the formula (I) is excellent in response characteristics such as temperature-dependence of response speed and low-temperature operation characteristic.

In order to enlarge a mesomorphic temperature range and improve response characteristics of a resultant liquid crystal composition, $R^3$ constituting $R^1$ or $R^2$ in the formula (I) may preferably be any one of the following groups (v) to (xi):

(v) $n\text{-}C_aH_{2a+1}-Y^3-$, (vi) 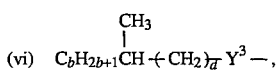

(vii) 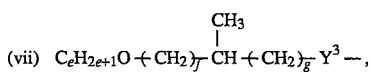

(viii) $C_hF_{2h+1}-(CH_2)_i-Y^3-$, (ix) 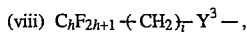

(x) $F-$, and (xi) $H-$, wherein a is an integer of 1–17; d, g and i are an integer of 0–7; b, e and h are integer of 1–9; f is 0 or 1; j is an integer of 1–16; $Y^3$ is a single bond, $-O-$, $-OCO-$ or $-COO-$; and $Y^4$ is $-CH_2O-$ or $-COO-$.

$R^3$ may be a cyclized alkyl group as described above. Herein, "cyclized alkyl group" means a cyclic alkyl group or an alkyl group having a partially cyclized structure in which the cyclized structure can be constituted by methylene group and/or at least one heteroatom (e.g., oxygen) and at least one methylene group in the alkyl group can be replaced with $-O-$ or $-CO-$.

The mesomorphic compound of the formula (I) may be an optically active compound or optically inactive compound. The mesomorphic compound of the formula (I) may preferably be an optically inactive compound.

The mesomorphic compound of the formula (I) may generally be synthesized through, e.g., the following reaction schemes ① to ④.

① 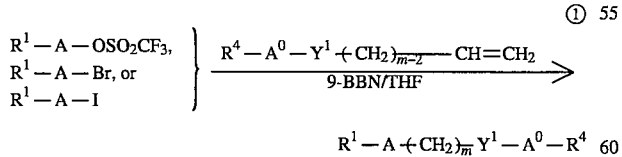

② 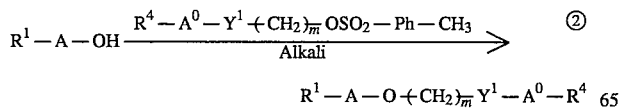

③ 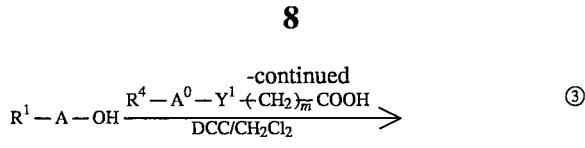

④ 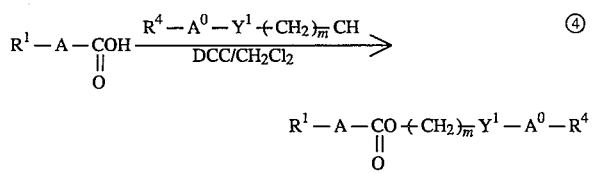

9-BBN: 9-borabicyclo[3,3,1]nonane?
DCC: 1,3-dicyclohexylcarbodiimide?
Ph: 1,4-phenylene?

In the above reaction schemes, $R^1$, $R^4$, A, $A^0$ $Y^1$, $Y^2$ and m have the same meanings as those described above.

It is possible to synthesize the mesomorphic compound of the formula (I) by connecting $-Y^2-(CH_2)_m-Y^1-A^0-R^1$ with A in advance and by further connecting $R^1$ therewith. It is also possible to obtain the mesomorphic compound of the formula (I) by finally forming A through ring closure.

Herein, the term "mesomorphic compound" covers not only a compound assuming a mesomorphic (liquid crystal) phase but also a compound not assuming a mesomorphic phase per se as long as a liquid crystal composition containing such a compound assumes a mesomorphic phase.

Specific examples of the mesomorphic compound of the formula (I) may include those represented by the following structural formulae including abbreviations for respective cyclic groups listed below.

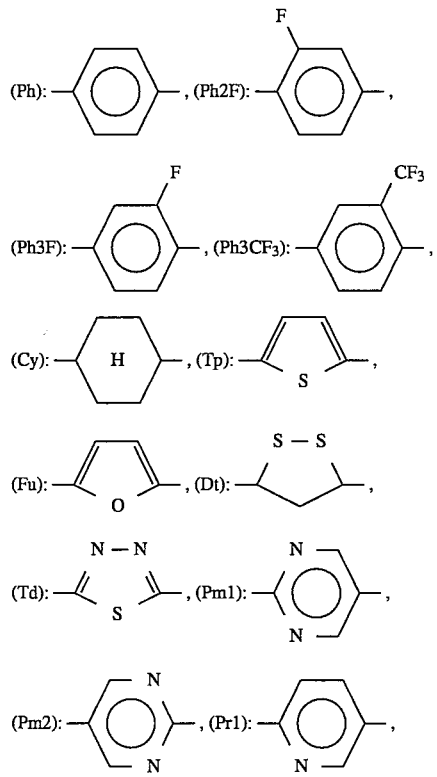

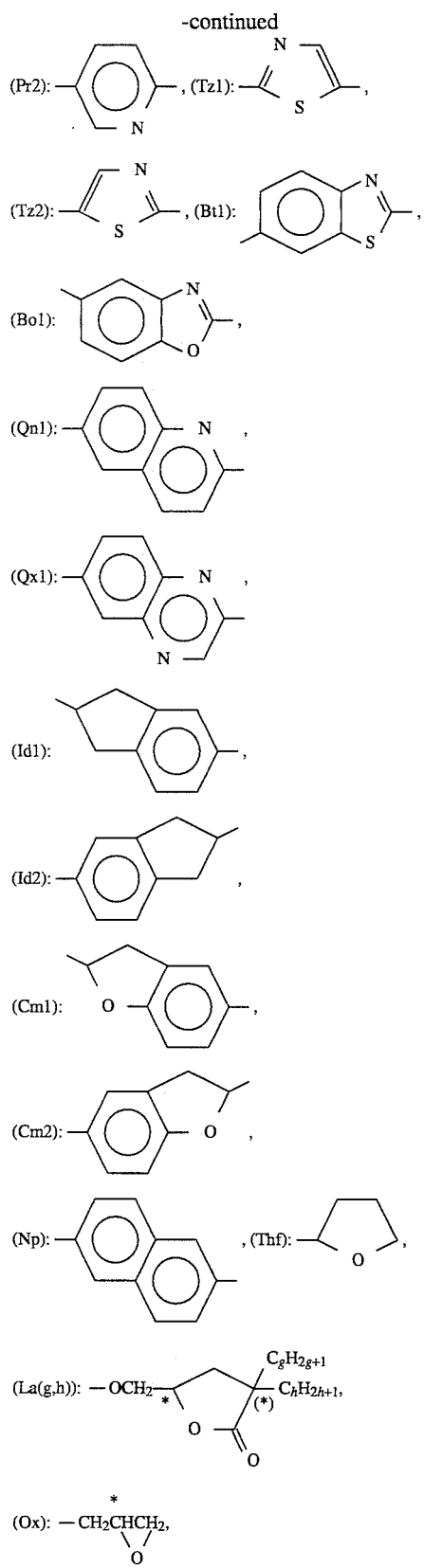

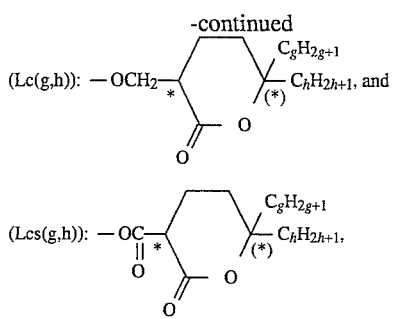

wherein g and h independently denote an integer of 0–10 provided that $g+h \leq 10$, and * denotes the location of an optically active center.

| | |
|---|---|
| $C_7H_{15}$—(Bt1)—(Ph)—$(CH_2)_4$—(Ph)—H | (I-1) |
| $C_{11}H_{23}$—(Bt1)—(Ph)—O—$(CH_2)_6$—(Ph)—H | (I-2) |
| $C_6H_{13}$—(Bt1)—(Ph)—$(CH_2)_{10}$—(Ph)—$C_4H_9$ | (I-3) |
| $C_8H_{17}$—(Bt1)—(Ph)—O—$(CH_2)_3$—(Ph)—H | (I-4) |
| $C_8H_{17}$—(Bt1)—(Ph)—O—$(CH_2)_5$—(Ph)—H | (I-5) |
| $C_6H_{13}$—(Bt1)—(Ph)—O—$(CH_2)_3$—(Ph)—H | (I-6) |
| $C_6H_{13}$—(Bt1)—(Ph)—O—$(CH_2)_5$—(Ph)—H | (I-7) |
| $C_8H_{17}$—(Bt1)—(Ph)—O—$(CH_2)_3$—(Cy)—H | (I-8) |
| $C_6H_{13}$—(Bt1)—(Ph)—O—$(CH_2)_3$—(Cy)—H | (I-9) |
| $C_8H_{17}$—(Bt1)—(Ph)—O—$(CH_2)_5$—(Cy)—H | (I-10) |
| $C_6H_{13}$—(Bt1)—(Ph)—O—$(CH_2)_5$—(Cy)—H | (I-11) |
| $C_4H_9$—(Bt1)—(Ph)—O—$(CH_2)_7$—(Cy)—$C_3H_7$ | (I-12) |
| $C_9H_{19}$—(Bt1)—(Ph)—$(CH_2)_5$—(Cy)—$C_6H_{13}$ | (I-13) |
| $C_5H_{11}$—(Bt1)—(Ph)—O—$(CH_2)_4$—(Tp)—H | (I-14) |
| $C_8H_{17}$—(Bt1)—(Ph)—O—$(CH_2)_5$—(Tp)—H | (I-15) |
| $C_4H_9$—(Bt1)—(Ph)—O—$(CH_2)_6$—(Fu)—H | (I-16) |
| $C_6H_{13}$—(Bt1)—(Ph)—O—$(CH_2)_3$—(Fu)—H | (I-17) |
| $C_8H_{17}$—(Bt1)—(Ph)—$(CH_2)_6$—(Tp)—$CH_3$ | (I-18) |
| $C_{10}H_{21}$—(Bt1)—(Ph)—$(CH_2)_8$—O—(Ph3F)—H | (I-19) |
| $C_8H_{17}O$—(Bt1)—(Ph)—O—$(CH_2)_4$—O—(Ph)—H | (I-20) |
| $C_9H_{19}$—(Bt1)—(Ph)—$(CH_2)_5$—O—(Ph)—F | (I-21) |
| $C_{11}H_{23}$—(Bt1)—(Ph)—O—$(CH_2)_5$—(Ph)—$CF_3$ | (I-22) |
| $C_7H_{15}O$—(Bt1)—(Ph)—O—$(CH_2)_5$—(Ph)—$CH_3$ | (I-23) |
| $C_{10}H_{21}$—(Bt1)—(Ph3F)—O—$(CH_2)_6$—(Cy)—H | (I-24) |
| $C_3H_7$—(Bt1)—(Ph)—$(CH_2)_{10}$—(Cy)—$CH_3$ | (I-25) |
| $C_{12}H_{25}$—(Bt1)—(Ph)—O—$(CH_2)_7$—(Ph)—$OCH_3$ | (I-26) |
| $C_6H_{13}$—(Bt1)—(Ph3F)—O—$(CH_2)_5$—(Tp)—H | (I-27) |
| $C_6H_{13}$—(Bt1)—(Ph)—O—$(CH_2)_3$—(Np)—H | (I-28) |
| $C_6H_{13}$—(Bt1)—(Ph)—O—$(CH_2)_5$—(Pr1)—H | (I-29) |
| $C_8H_{17}$—(Bt1)—(Ph)—O—$(CH_2)_3$—O—(Pr2)—H | (I-30) |
| $C_6H_{13}$—(Bt1)—(Ph)—O—$(CH_2)_3$—(Id2)—H | (I-31) |
| $C_6H_{13}$—(Bo1)—(Ph)—O—$(CH_2)_5$—(Ph)—H | (I-32) |

| | |
|---|---|
| $C_{10}H_{21}-(Bo1)-(Ph)-O+CH_2\frac{1}{3}(Cy)-H$ | (I-33) |
| $C_4H_9-(Bo1)-(Ph)-COO+CH_2\frac{1}{3}(Ph)-H$ | (I-34) |
| $C_{13}H_{27}-(Bo1)-(Ph)-COO+CH_2\frac{1}{3}(Ph)-F$ | (I-35) |
| $C_9H_{19}-(Bo1)-(Ph)+CH_2\frac{1}{4}(Cy)-CH_3$ | (I-36) |
| $C_5H_{11}-(Bo1)-(Np)-O+CH_2\frac{1}{4}(Cy)-H$ | (I-37) |
| $C_8H_{17}-(Bo1)-(Np)-O+CH_2\frac{1}{4}(Ph)-H$ | (I-38) |
| $C_{11}H_{23}-(Bo1)-(Np)+CH_2\frac{1}{6}O-(Ph)-CF_3$ | (I-39) |
| $C_6H_{13}-(Ph)-(Tz1)-(Ph)-O+CH_2\frac{1}{4}(Ph)-H$ | (I-40) |
| $C_6H_{13}-(Ph)-(Tz1)-(Ph)-OCO+CH_2\frac{1}{3}(Ph)-H$ | (I-41) |
| $C_9H_{19}-(Ph)-(Tz1)-(Ph)-O+CH_2\frac{1}{6}(Ph)-H$ | (I-42) |
| $C_4H_9-(Ph2F)-(Tz1)-(Ph)-O+CH_2\frac{1}{5}(Ph)-H$ | (I-43) |
| $C_5H_{11}-(Ph)-(Tz1)-(Ph)-OCO+CH_2\frac{1}{4}(Ph)-H$ | (I-44) |
| $C_8H_{17}-(Ph)-(Tz1)-(Ph)+CH_2\frac{1}{3}O-(Ph)-F$ | (I-45) |
| $C_4H_9-(Ph)-(Tz1)-(Ph)+CH_2\frac{1}{6}(Ph)-C_5H_{11}$ | (I-46) |
| $C_{11}H_{23}-(Ph)-(Ph3F)+CH_2\frac{1}{4}O-(Ph)-H$ | (I-47) |
| $C_7H_{15}-(Ph)-(Tz1)-(Ph3F)+CH_2\frac{1}{8}(Tp)-H$ | (I-48) |
| $C_3H_7-(Ph)-(Tz1)-(Ph)-O+CH_2\frac{1}{5}(Tp)-H$ | (I-49) |
| $C_6H_{13}-(Ph)-(Tz1)-(Ph)+CH_2\frac{1}{4}(Cy)-H$ | (I-50) |
| $C_8H_{17}-(Ph)-(Tz1)-(Ph)-O+CH_2\frac{1}{7}(Cy)-H$ | (I-51) |
| $C_6H_{13}-(Ph)-(Tz1)-(Ph)-OCO+CH_2\frac{1}{4}(Cy)-H$ | (I-52) |
| $C_5H_{11}-(Ph)-(Tz1)-(Ph)-OCO+CH_2\frac{1}{3}(Cy)-C_4H_9$ | (I-53) |
| $C_{10}H_{21}-O-(Ph)-(Tz1)-(Ph)+CH_2\frac{1}{5}(Cy)-C_3H_7$ | (I-54) |
| $C_4H_9-(Ph)+CH_2\frac{1}{5}(Ph)-(Tz1)-(Ph)-C_{12}H_{25}$ | (I-55) |
| $H-(Ph2F)+CH_2\frac{1}{8}(Ph)-(Tz1)-(Ph3F)-OC_5H_{11}$ | (I-56) |
| $C_6H_{13}-(Tp)+CH_2\frac{1}{6}(Ph)-(Tz1)-(Ph2F)-C_{11}H_{23}$ | (I-57) |
| $H-(Cy)+CH_2\frac{1}{6}(Ph)-(Tz1)-(Ph)-C_9H_{19}$ | (I-58) |
| $C_{12}H_{25}-(Tz1)-(Ph)-OCO+CH_2\frac{1}{4}(Ph)-H$ | (I-59) |
| $C_6H_{13}-(Tz1)-(Ph)-O+CH_2\frac{1}{10}(Ph)-CH_3$ | (I-60) |
| $C_{10}H_{21}-(Tz1)-(Ph)-O+CH_2\frac{1}{3}(Cy)-H$ | (I-61) |
| $C_4H_9-(Tz1)-(Ph)-O+CH_2\frac{1}{5}(Cy)-H$ | (I-62) |
| $C_6H_{13}-(Tz1)-(Ph)-O+CH_2\frac{1}{5}(Cy)-C_3H_7$ | (I-63) |
| $C_8H_{17}-(Tz1)-(Ph3F)+CH_2\frac{1}{8}(Ph)-OC_2H_5$ | (I-64) |
| $C_5H_{11}-(Tz1)-(Ph2F)+CH_2\frac{1}{5}O-(Ph)-F$ | (I-65) |
| $C_{11}H_{23}-(Tz1)-(Ph3CF_3)-O+CH_2\frac{1}{4}(Ph)-H$ | (I-66) |
| $C_{10}H_{21}-(Pm2)-(Ph)-OCO+CH_2\frac{1}{4}(Dt)-H$ | (I-67) |
| $C_6H_{13}O-(Pm2)-(Ph)-O+CH_2\frac{1}{6}(Dt)-H$ | (I-68) |
| $C_8H_{17}-(Pm2)-(Ph3F)+CH_2\frac{1}{10}(Dt)-H$ | (I-69) |
| $C_{10}H_{21}-(Ph)-COO-(Ph)+CH_2\frac{1}{4}(Id2)-C_5H_{11}$ | (I-70) |
| $C_3H_7-(Cy)-CH_2O-(Ph)+CH_2\frac{1}{6}(Id2)-C_6H_{13}$ | (I-71) |
| $C_4H_9-(Ph)-C\equiv C-(Ph)+CH_2\frac{1}{4}(Cm2)-C_{10}H_{21}$ | (I-72) |
| $C_8H_{17}-(Ph)-COS-(Ph)+CH_2\frac{1}{9}(Id2)-H$ | (I-73) |
| $C_6H_{13}O-(Ph2F)-CH=CH-(Ph)+CH_2\frac{1}{5}(Cm2)-C_8H_{17}$ | (I-74) |
| $C_{10}H_{21}-(Id1)-(Pm1)-O+CH_2\frac{1}{3}(Ph)-H$ | (I-75) |
| $C_7H_{15}-(Id1)-(Pm1)-O+CH_2\frac{1}{6}(Ph)-H$ | (I-76) |
| $C_{11}H_{23}-(Id1)-(Pm1)+CH_2\frac{1}{5}(Ph)-F$ | (I-77) |
| $C_5H_{11}-(Id1)-(Pm1)+CH_2\frac{1}{7}O-(Ph)-H$ | (I-78) |
| $C_8H_{17}-(Id1)-(Pm1)-O+CH_2\frac{1}{5}(Ph)-CF_3$ | (I-79) |
| $C_7H_{15}-(Id1)-(Pm1)+CH_2\frac{1}{6}(Ph)-OC_4H_9$ | (I-80) |
| $C_8H_{17}-(Id1)-(Pm1)-O+CH_2\frac{1}{4}(Cy)-H$ | (I-81) |
| $C_9H_{19}-(Id1)-(Pm1)-O+CH_2\frac{1}{5}(Tp)-C_3H_7$ | (I-82) |
| $C_{12}H_{25}-(Id1)-(Pm1)-OCO+CH_2\frac{1}{3}(Tp)-H$ | (I-83) |
| $C_{10}H_{21}-(Cm1)-(Pm1)-O+CH_2\frac{1}{7}(Ph)-CH_3$ | (I-84) |
| $C_5H_{11}-(Cm1)-(Pm1)+CH_2\frac{1}{4}(Ph)-H$ | (I-85) |
| $C_6H_{13}-(Cm1)-(Pm1)-O+CH_2\frac{1}{5}(Cy)-H$ | (I-86) |
| $C_{11}H_{23}-(In1)-(Pr1)-O+CH_2\frac{1}{8}(Cy)-C_5H_{11}$ | (I-87) |
| $C_{12}H_{25}-(Cm1)-(Pr1)-O+CH_2\frac{1}{9}(Ph)-H$ | (I-88) |
| $C_6H_{13}O-(Qn1)-(Ph)+CH_2\frac{1}{4}O-(Ph)-H$ | (I-89) |
| $C_{12}H_{25}O-(Qn1)-(Ph)-O+CH_2\frac{1}{4}O-(Ph)-H$ | (I-90) |
| $H-(Ph)+CH_2\frac{1}{5}O-(Qn1)-(Ph)-C_5H_{11}$ | (I-91) |
| $H-(Ph)-O+CH_2\frac{1}{3}O-(Qn1)-(Ph)-C_7H_{15}$ | (I-92) |
| $H-(Ph)+CH_2\frac{1}{6}(Qn1)-(Ph)-C_9H_{19}$ | (I-93) |
| $H-(Cy)+CH_2\frac{1}{7}O-(Qn1)-(Ph)-C_6H_{13}$ | (I-94) |
| $H-(Fu)+CH_2\frac{1}{9}O-(Qn1)-(Ph)-C_4H_9$ | (I-95) |
| $C_4H_9-(Tp)+CH_2\frac{1}{3}O-(Qn1)-(Ph)-C_8H_{17}$ | (I-96) |
| $H-(Ph)+CH_2\frac{1}{6}O-(Qx1)-(Ph)-OC_3H_7$ | (I-97) |
| $H-(Ph)-O+CH_2\frac{1}{10}(Qx1)-(Ph)-C_6H_{13}$ | (I-98) |
| $CH_3O-(Ph)-O+CH_2\frac{1}{10}(Qx1)-(Ph)-C_6H_{13}$ | (I-100) |
| $H-(Ph2F)+CH_2\frac{1}{4}O-(Qx1)-(Ph)-C_9H_{19}$ | (I-101) |
| $H-(Tp)+CH_2\frac{1}{5}O-(Qx1)-(Ph)-C_5H_{11}$ | (I-102) |
| $C_3H_7-(Cy)+CH_2\frac{1}{3}O-(Qn1)-(Ph)-C_5H_{11}$ | (I-103) |
| $H-(Cy)+CH_2\frac{1}{8}(Qn1)-(Ph)-OC_2H_5$ | (I-104) |
| $H-(Fu)+CH_2\frac{1}{4}O-(Qx1)-(Ph)-C_8H_{17}$ | (I-105) |
| $C_8F_{17}-(Ph)-O+CH_2\frac{1}{5}(Bt1)-(Ph)-O+CH_2\frac{1}{2}CH=CH_2$ | (I-106) |
| $C_2H_5CH(CH_3)CH_2-(Bt1)-(Ph)-O+CH_2\frac{1}{5}(Cy)-H$ | (I-107) |
| $C_6H_{13}C^*H(F)CH_2O-(Bt1)-(Ph)+CH_2\frac{1}{3}O-(Ph)-H$ | (I-108) |
| $H+Cy)+CH_2\frac{1}{4}O+Bt1)-(Ph)-O+CH_2\frac{1}{2}C^*H(CF_3)C_4H_9$ | (I-109) |
| $H-(Ph)+CH_2\frac{1}{7}COO-(Bt1)-(Ph)-OCH_2C_6H_{13}$ | (I-110) |
| $C_3F_7CH_2O-(Bt1)-(Ph3F)+CH_2\frac{1}{5}(Ph)-OCH_3$ | (I-111) |
| $H-(Ph)+CH_2\frac{1}{6}O-(Bo1)-(Ph)-CH_2C^*H(CH_3)OC_2H_5$ | (I-112) |
| $C_5F_{11}+CH_2\frac{1}{2}O-(Bo1)-(Ph)+CH_2\frac{1}{8}(Cy)-H$ | (I-113) |
| $H-(Ph)+CH_2\frac{1}{7}(Bo1)-(Ph)-C_6F_{13}$ | (I-114) |
| $H-(Cy)+CH_2\frac{1}{5}OCO-(Bo1)-(Np)-CH_2CH+CH_3)_2$ | (I-115) |
| $C_3H_7CH(CH_3)CH_2-(Ph)-(Tz1)-(Ph)-O+CH_2\frac{1}{6}(Cy)-H$ | (I-116) |
| $H-(Ph)+CH_2\frac{1}{8}(Tz1)-(Ph)-OCH_2C^*H(F)C_5H_{11}$ | (I-117) |
| $H-(Cy)+CH_2\frac{1}{5}(Tz1)-(Ph)-OCH_2C_7F_{15}$ | (I-118) |
| $F-(Ph)-O+CH_2\frac{1}{5}(Tz1)-(Ph)-O+CH_2\frac{1}{3}O-CH_3$ | (I-119) |

-continued $CH_2=CH+CH_2\}_5(Tz1)-(Ph)-O+CH_2\}_4(Cy)-CH_3$ (I-120)

$C_3H_7-(Tz1)-(Ph)-O+CH_2\}_3(Ph)-C_3F_7$ (I-121)

$C_6H_{13}CH(CH_3)-(Tz1)-(Ph)-OCO+CH_2\}_3(Ph)-H$ (I-122)

$H-(Ph)+CH_2\}_{10}(Qn1)-(Ph)-OC^*H(CF_3)C_6H_{13}$ (I-123)

$C_2H_5CH(CH_3)CH_2O-(Qn1)-(Ph)+CH_2\}_6(Cy)-C_3H_7$ (I-124)

$C_2H_5C^*H(F)COO-(Qn1)-(Ph)+CH_2\}_5O-(Ph)-H$ (I-125)

$H-(Cy)+CH_2\}_4O-(Qn1)-(Ph3F)-CH_2+CF_2\}_7H$ (I-126)

$C_2H_5OCH_2CH(CH_3)O-(Qx1)-(Ph)+CH_2\}_5(Ph)-F$ (I-127)

$H-(Ph)-O+CH_2\}_7(Qx1)-(Ph)-O+CF_2\}_5H$ (I-128)

$H-(Cy)+CH_2\}_4O-(Qx1)-(Ph)-OCH_2C^*H(F)C_8H_{17}$ (I-129)

$C_4H_9C^*H(CF_3)CH_2COO-(Qx1)-(Ph)+CH_2\}_5(Cy)-H$ (I-130)

$C_2F_5-(Ph)-O+CH_2\}_3(Qx1)-(Ph)-C_6H_{13}$ (I-131)

$H-(Ph)+CH_2\}_7(Qx1)-(Ph)-O+CH_2\}_2C^*H(CH_3)C_3H_7$ (I-132)

$C_6H_{13}-(Ph)-(Tz1)-(Ph)-OCO+CH_2\}_4(Cy)-C_4H_9$ (I-133)

$C_7H_{15}-(Qx1)-(Ph)+CH_2\}_6(Cy)-H$ (I-134)

$C_9H_{19}-(Ph)-(Tz1)-(Ph)-OCO+CH_2\}_5(Ph3F)-H$ (I-135)

$C_{10}H_{21}-(Td)-(Ph)-O+CH_2\}_5(Cy)-H$ (I-136)

$C_6H_{13}-(Ph)-(Td)-(Ph)+CH_2\}_3(Ph)-F$ (I-137)

$C_{11}H_{23}O-(Pm2)-(Ph)-O+CH_2\}_4(Fu)-H$ (I-138)

$H-(Cy)+CH_2\}_4(Tz1)-(Ph)-O+CH_2\}_5(Cy)-H$ (I-139)

$H-(Id1)-(Ph)+CH_2\}_{10}(Ph)-CH_2CH(CH_3)C_2H_5$ (I-140)

$CH_3-(Bt1)-(Ph)+CH_2\}_3OCO-(Cy)-H$ (I-141)

$C_2H_6-(Ph)-COO-(Qn1)-(Ph)+CH_2\}_3(Cy)-H$ (I-142)

$C_{13}H_{27}-(Bt1)-(Ph)+CH_2\}_4(Ph)-H$ (I-143)

$C_{14}H_{29}-(Bo1)-(Np)+CH_2\}_3COO-(Ph)-H$ (I-144)

$C_{15}H_{31}-(Ph)-(Tz1)-(Ph)-O+CH_2\}_2O-(Ph)-H$ (I-145)

$C_{16}H_{33}-(Cm1)-(Pm1)+CH_2\}_5(Ph)-H$ (I-146)

$C_{17}H_{35}-(Bo1)-(Ph)-O+CH_2\}_2(Cy)-H$ (I-147)

$C_{18}H_{37}-(In1)-(Ph)+CH_2\}_3(Cy)-CH_3$ (I-148)

$H-(Thf)-(Tz1)-(Ph)+CH_2\}_4(Cy)-H$ (I-149)

$C_{10}H_{21}S-(Ph)-COO-(Ph)-(Tz2)+CH_2\}_{11}(Cy)-H$ (I-150)

$C_6H_{13}C\equiv C-(Ph)-(Tz1)-(Ph)+CH_2\}_4(Cy)-H$ (I-151)

$C_2H_5CH(CN)+CH_2\}_2O-(Bt1)-(Ph)+CH_2\}_6(Cy)-H$ (I-152)

$CH_3-(Ph)-(Tz1)-(Ph)-O+CH_2\}_3(Cy)-C_{11}H_{23}$ (I-153)

$F-(Ph)-COO-(Qx1)-(Ph)+CH_2\}_{12}(Cy)-H$ (I-154)

$H-(Cm1)-(Ph)+CH_2\}_4(Ph)-C_{12}H_{25}$ (I-155)

$C_6H_{13}-(Qx1)-(Ph)+CH_2\}_3(Ph)-SCO-C_8H_7$ (I-156)

-continued $C_5H_{11}-(Tz)-(Ph)+CH_2\}_5(Ph)+CH_2\}_2CH=CHC_3H_7$ (I-157)

$C_4H_9-(Bt1)-(Ph)+CH_2\}_{13}(Ph)-C\equiv CC_5H_{11}$ (I-158)

$C_6H_{13}-(Bo1)-(Ph)+CH_2\}_5(Ph3M)-OCH_2CH(CN)C_2H_5$ (I-159)

$C_{10}H_{21}-(Qn1)-OCH_2-(Ph2M)+CH_2\}_4(Cy)-H$ (I-160)

$C_8H_{17}-(Ph)-SCO-(Qx1)+CH_2\}_6(Cy)-H$ (I-161)

$C_6H_{13}-(Cy)-COO-(Ph)-(Tz2)+CH_2\}_5(Cy)-H$ (I-162)

$C_{10}H_{21}-(Tz2)-(Ph)-(Pm1)+CH_2\}_{13}(Cy)-H$ (I-163)

$C_3H_7-(Cy)-CH_2O-(Qn1)-(Ph)-O+CH_2\}_6(Cy)-H$ (I-164)

$C_4H_9-(Ph)-OCH_2-(Ph)-(Tz2)+CH_2\}_{10}(Cy)-H$ (I-165)

$C_6H_{13}-(Ph)-COO-(Qx1)-(Ph)-OCO+CH_2\}_3(Cy)-H$ (I-166)

$C_4H_9-(Ph)-OCO-(Ph)-(Tz1)+CH_2\}_5(Ph)-H$ (I-167)

$C_7H_{15}-(Qn1)-(Ph)-COS-(Ph)+CH_2\}_5(Cy)-H$ (I-168)

$C_9H_{19}-(Id1)-(Ph)-SCO-(Ph)+CH_2\}_3(Ph)-F$ (I-169)

$C_8H_{17}-(Tz1)-(Ph)-C\equiv C-(Ph)+CH_2\}_2OCO-(Cy)-H$ (I-170)

$C_6H_{13}-(Tz2)-(Ph)-CH=CH+Ph)-O+CH_2\}_4O+Ph)-H$ (I-171)

$CH_3-(Qn1)-(Ph)O+CH_2\}_{17}(Ph)-H$ (I-172)

$C_3H_7-(Qx1)-(Ph)-OCO+CH_2\}_{16}(Cy)-H$ (I-173)

$C_5H_{11}-(Tz1)-(Ph)-O+CH_2\}_{14}O-(Ph3M)-H$ (I-174)

$C_7H_{15}-(Id1)-(Py1)+CH_2\}_{14}COO-(Ph)-H$ (I-175)

$C_6H_{13}-(Ph)-(Tz1)-(Ph)+CH_2\}_{12}(Cy)-H$ (I-176)

$H-(Ph)+CH_2\}_4(Qn1)-(Ph)-(Ox)$ (I-177)

$H-(Ph)+CH_2\}_4(Qn1)-(Ph)-(La(3,0))$ (I-178)

$H-(Ph)+CH_2\}_4(Qn1)-(Ph)-(Lcs(5,0))$ (I-179)

$H-(Ph)+CH_2\}_4(Qn1)-(Ph)-(Lc(1,1))$ (I-180)

The liquid crystal composition according to the present invention may be obtained by mixing at least one species of the mesomorphic compound represented by the formula (I) and at least one species, preferably 1–50 species, more preferably 1–30 species, particularly 3–30 species, of another mesomorphic compound, in appropriate proportions determined by taking account of usage or uses of a liquid crystal device using the composition, characteristics required therefor, etc.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those denoted by the following formulae (III) to (XII).

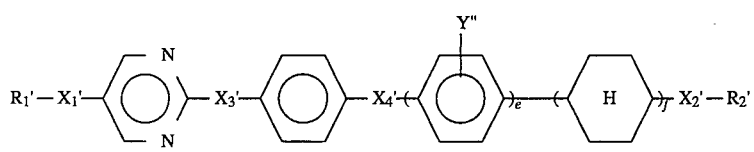

(III)

wherein e denotes 0 or 1 and f denotes 0 or 1 with proviso that e+f=0 or 1; Y" denotes H, halogen, CH₃ or CF₃; and $X_1'$ and $X_2'$ respectively denote a single bond,

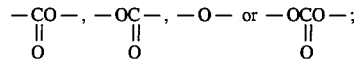

$X_3'$ and $X_4'$ respectively denote a single bond,

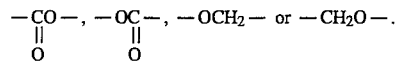

In the formula (III), preferred compounds thereof may include those represented by the following formulas (IIIa) to (IIIe):

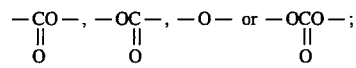

and $X_3'$, $X_4'$ and $X_5'$ respectively denote a single bond,

In the formula (IV), preferred compounds thereof may include those represented by the following formulas (IVa) to (IVc):

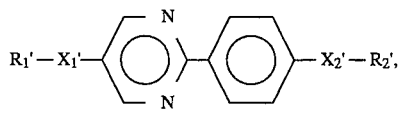
(IIIa)

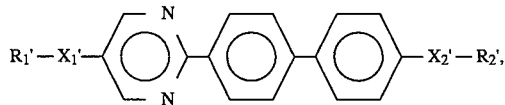
(IIIb)

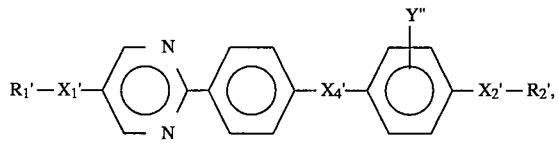
(IIIc)

and

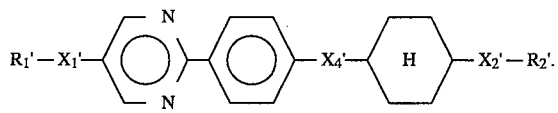
(IIId)

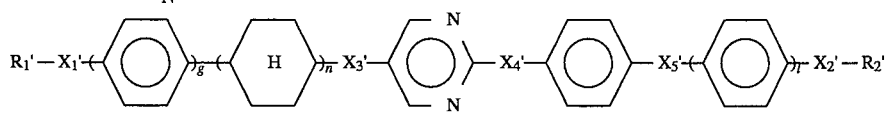
(IV)

wherein g and h respectively denote 0 or 1 with proviso that g+h=0 or 1; i denotes 0 or 1; $X_1'$ and $X_2'$ respectively denote a single bond,

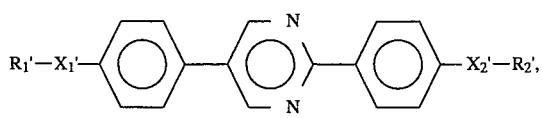
(IVa)

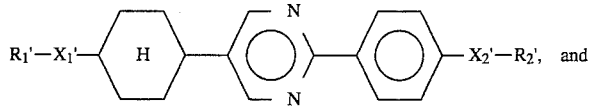
(IVb)

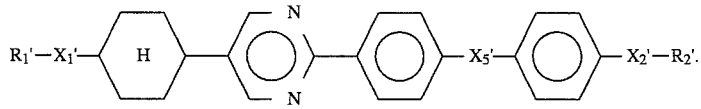
(IVc)

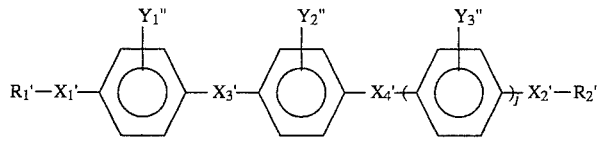
(V)

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

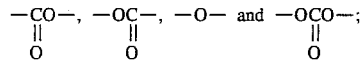

and $X_3'$ and $X_4'$ respectively denote a single bond,

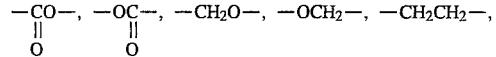

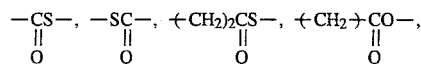

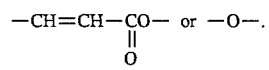

In the formula (V), preferred compounds thereof may include those represented by the following formulas (Va) and (Vb):

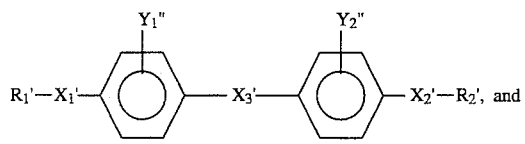
(Va)

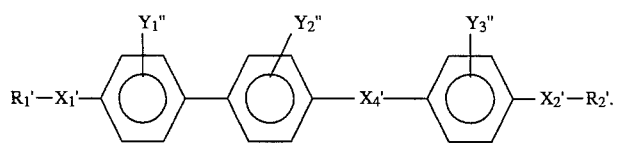
(Vb)

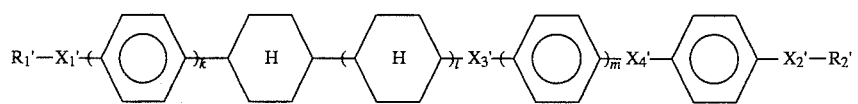
(VI)

wherein k, l and m respectively denote 0 or 1 with proviso that k+l+m=0, 1 or 2; $X_1'$ and $X_2'$ respectively denote a single bond, $$-CO-,\ -OC-,\ -O-\ \text{or}\ -OCO-;$$
$$\phantom{-CO}\|\phantom{-}\phantom{-OC}\|\phantom{-}\phantom{-O-\text{or}-OC}\|$$
$$\phantom{-C}O\phantom{--}\phantom{-O}O\phantom{----------}O$$

and $X_3'$ and $X_4'$ respectively denote a single bond, $$-CO-,\ -OC-,\ -CH_2O\ \text{or}\ -OCH_2-.$$

In the formula (VI), preferred compounds thereof may include those represented by the following formulas (VIa) to (VIf):

R₁'—X₁'—(H)—X₃'—(○)—(○)—X₂'—R₂', (VIa)

R₁'—X₁'—(H)—(H)—X₃'—(○)—X₂'—R₂', (VIb)

R₁'—X₁'—(H)—(H)—X₃'—(○)—(○)—X₂'—R₂', (VIc)

R₁'—X₁'—(H)—(○)—X₄'—(○)—X₂'—R₂', (VId)

-continued

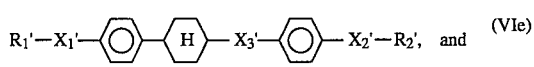 (VIe)

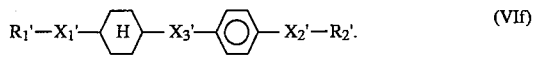 (VIf)

Herein, $R_1'$ and $R_2'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

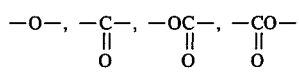

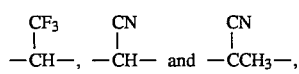

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH(CF$_3$)—.

Further, preferred examples of $R_1'$ and $R_2'$ may respectively include those represented by the following groups (i) to (ix):

i) a linear alkyl group having 1–15 carbon atoms;

ii) 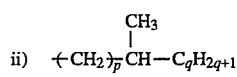

wherein p denotes an integer of 0–5 and q denotes an integer of 2–11 (optically active or inactive);

iii) 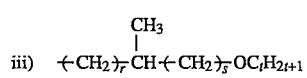

wherein r denotes an integer of 0–6, s denotes 0 or 1, and t denotes an integer of 1–14 (optically active or inactive);

iv) 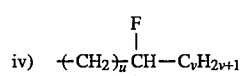

wherein u denotes 0 or 1 and v denotes an integer of 1–16;

v) 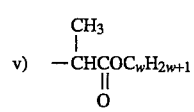

wherein w denotes an integer of 1–15 (optically active or inactive);

vi) 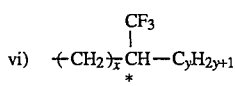

wherein x denotes an integer of 0–2 and y denotes an integer of 1–15;

vii) 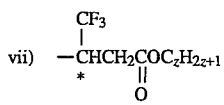

wherein z denotes an integer of 1–15;

viii) 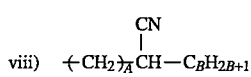

wherein A denotes an integer of 0–2 and B denotes an integer of 1–15 (optically active or inactive); and ix) 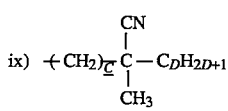

wherein C denotes an integer of 0–2 and D denotes an integer of 1–15 (optically active or inactive).

In the above-mentioned formulas (IIIa) to (IIId), more preferred compounds thereof may include those represented by the formulas (IIIaa) to (IIIdc):

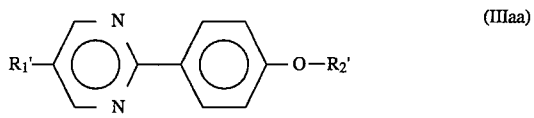 (IIIaa)

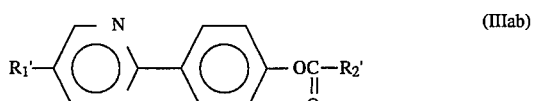 (IIIab)

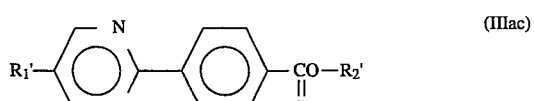 (IIIac)

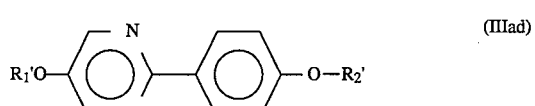 (IIIad)

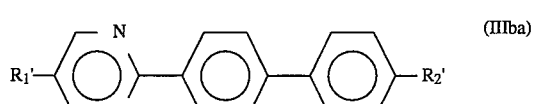 (IIIba)

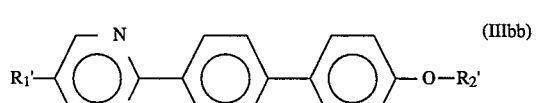 (IIIbb)

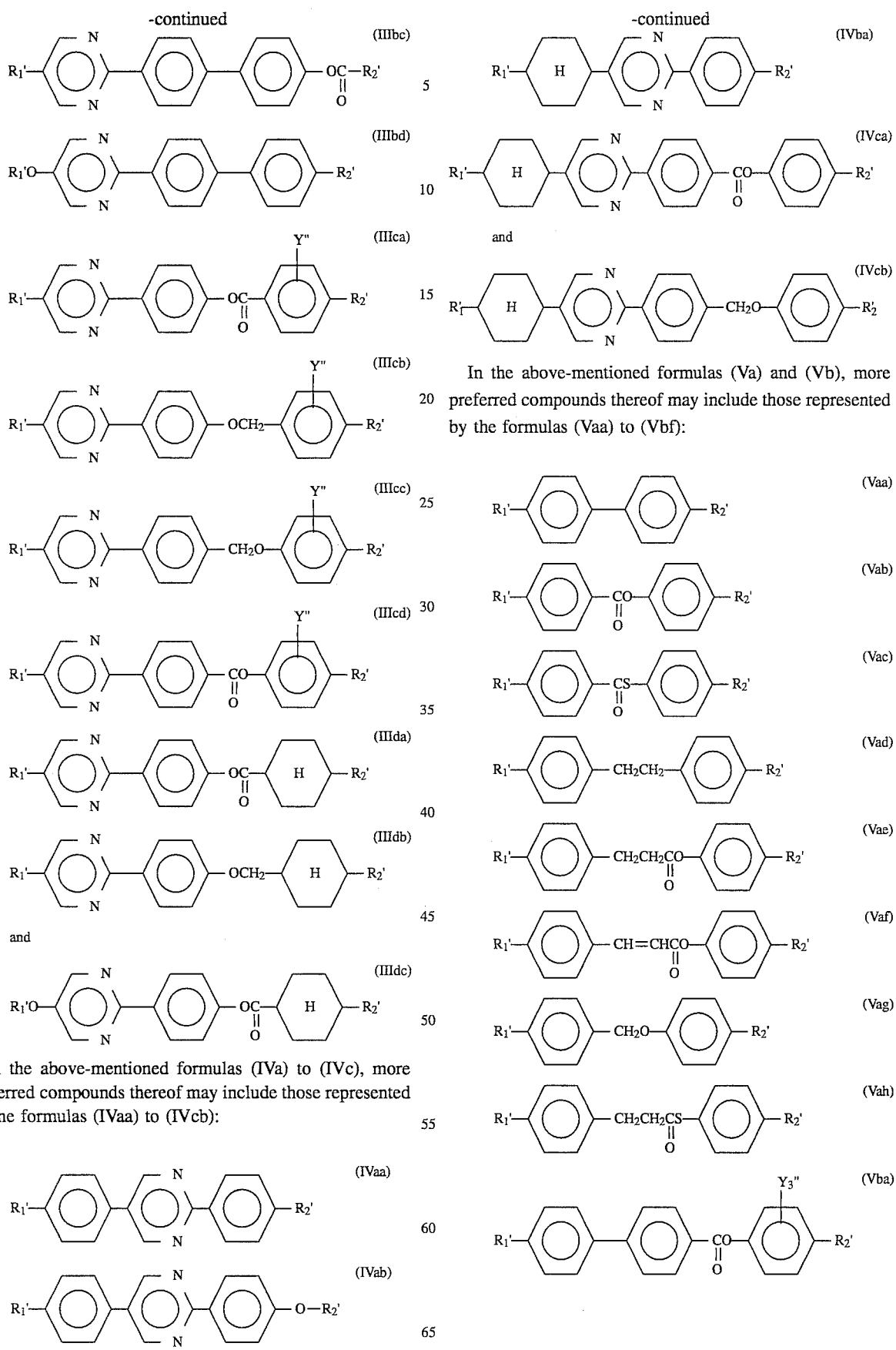

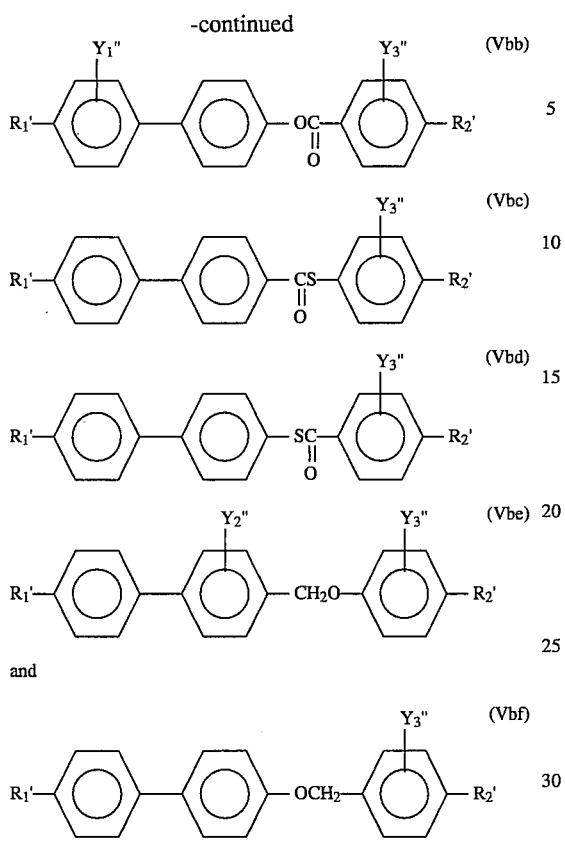

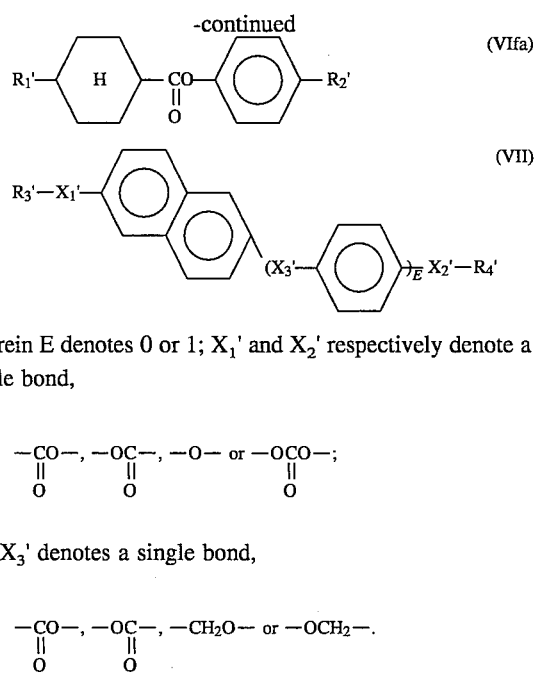

In the above-mentioned formulas (VIa) to (VIf), more preferred compounds thereof may include those represented by the formulas (VIaa) to (VIfa):

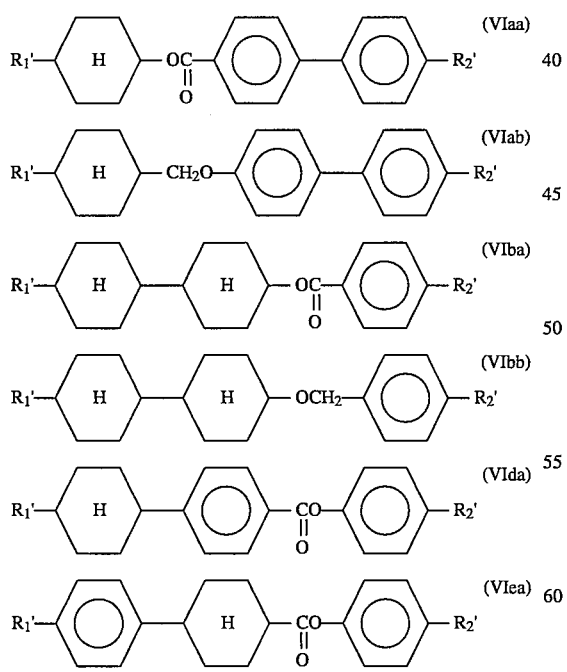

wherein E denotes 0 or 1; $X_1'$ and $X_2'$ respectively denote a single bond, $$-\underset{\underset{O}{\|}}{C}O-,\ -O\underset{\underset{O}{\|}}{C}-,\ -O-\ \text{or}\ -O\underset{\underset{O}{\|}}{C}O-;$$

and $X_3'$ denotes a single bond, $$-\underset{\underset{O}{\|}}{C}O-,\ -O\underset{\underset{O}{\|}}{C}-,\ -CH_2O-\ \text{or}\ -OCH_2-.$$

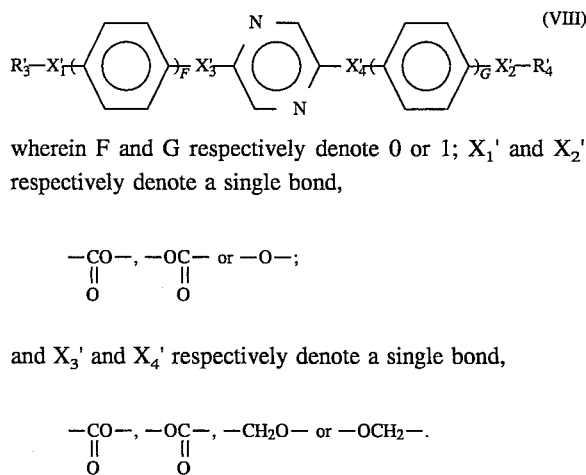

wherein F and G respectively denote 0 or 1; $X_1'$ and $X_2'$ respectively denote a single bond, $$-\underset{\underset{O}{\|}}{C}O-,\ -O\underset{\underset{O}{\|}}{C}-\ \text{or}\ -O-;$$

and $X_3'$ and $X_4'$ respectively denote a single bond, $$-\underset{\underset{O}{\|}}{C}O-,\ -O\underset{\underset{O}{\|}}{C}-,\ -CH_2O-\ \text{or}\ -OCH_2-.$$

In the above formula (VII), preferred compounds thereof may include those represented by the following formulas (VIIa) and (VIIb):

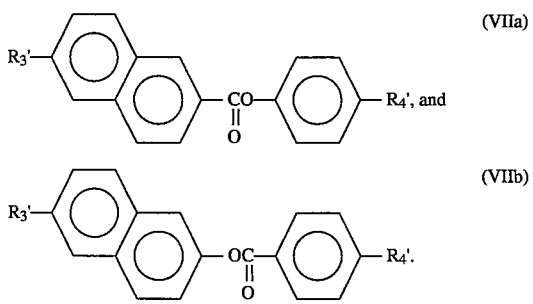

In the above formula (VIII), preferred compounds thereof may include those represented by the follwoing formulas (VIIIa) and (VIIIb).

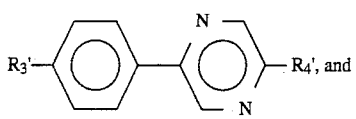 (VIIIa)

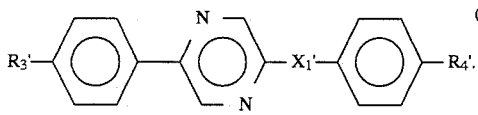 (VIIIb)

More preferred compounds of the formula (VIIIb) may include those represented by the formulas (VIIIba) to (VIIIbb):

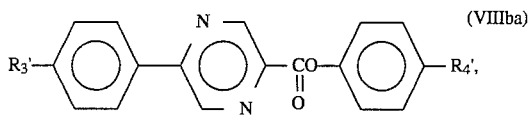 (VIIIba)

and

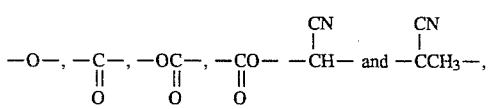 (VIIIbb)

Herein, $R_3'$ and $R_4'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

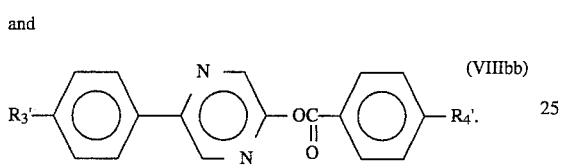

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1–15 carbon atoms;

ii) 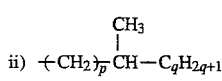

wherein p denotes an integer of 0–5 and q denotes an integer of 2–11 (optically active or inactive);

iii) 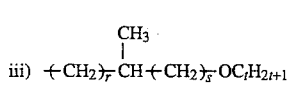

wherein r denotes an integer of 0–6, s denotes 0 or 1, and t denotes an integer of 1–14 (optically active or inactive);

iv) 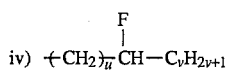

wherein u denotes an integer of 0 or 1 and v denotes an integer of 1–16 (optically active or inactive);

v) 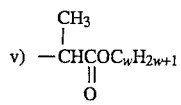

wherein w denotes an integer of 1–15 (optically active or inactive);

vi) 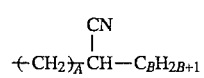

wherein A denotes an integer of 0–2 and B denotes an integer of 1–15 (optically active or inactive); and vii) 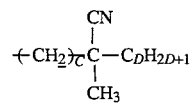

wherein C denotes an integer of 0–2 and D denotes an integer of 1–15 (optically active or inactive).

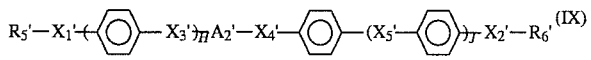 (IX)

wherein H and J respectively denote 0 or 1 with proviso that H+J=0 or 1; $X_1'$ and $X_2'$ respectively denote a single bond,

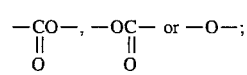

$A_2'$ denotes

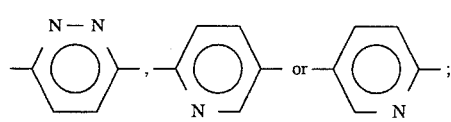

and $X_3'$ and $X_4'$ respectively denote a single bond,

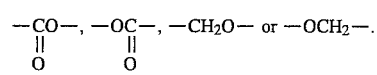

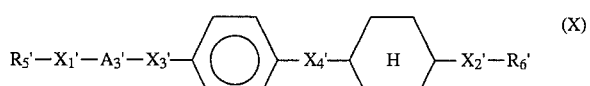 (X)

wherein $X_1'$ and $X_2'$ respectively denote a single bond,

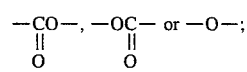

$A_3'$ denotes

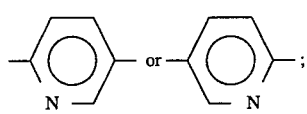

and $X_3'$ and $X_4'$ respectively denote a single bond,

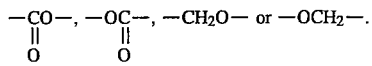

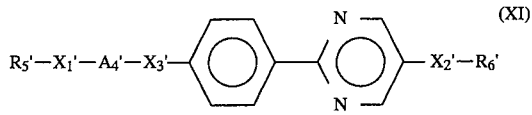

wherein $X_1'$ and $X_2'$ respectively denote a single bond,

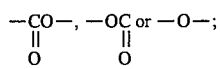

$A_4'$ denotes

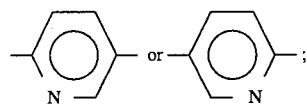

and $X_3'$ respectively denotes a single bond,

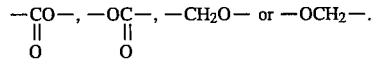

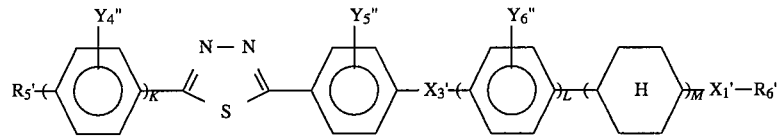

wherein K, L and M respectively denote 0 or 1 with the proviso that K+L+M=0 or 1; $X_1'$ denotes a single bond,

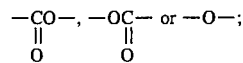

$X_3'$ denotes a single bond,

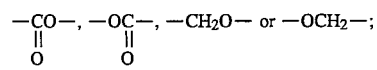

and $Y_4''$, $Y_5''$ and $Y_6''$ respectively denote H or F.

In the above formula (IX), preferred compounds thereof may include those represented by the following formulas (IXa) to (IXc):

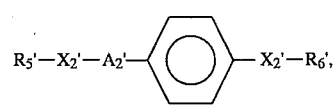

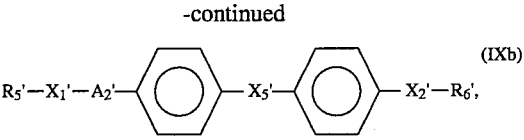

and

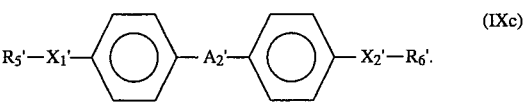

In the above formula (X), preferred compounds thereof may include those represented by the following formulas (Xa) and (Xb):

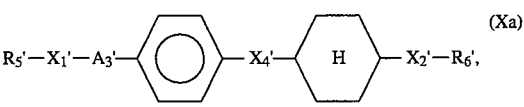

and

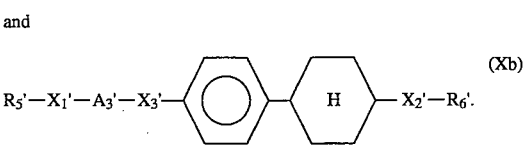

In the above formula (XII), preferred compounds thereof may include those represented by the following formulas (XIIa) and (XIId):

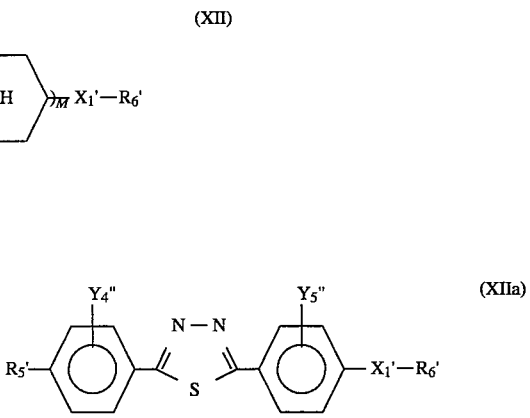

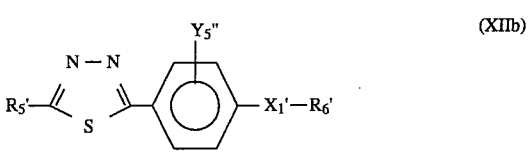

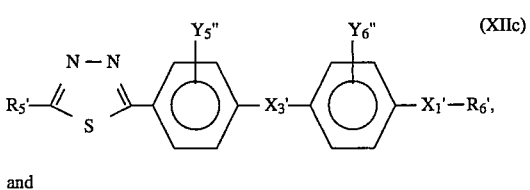

and

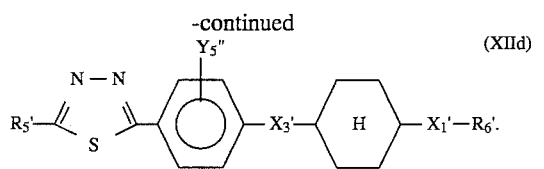
(XIId)

In the above-mentioned formulas (IXa) to (IXc), more preferred compounds thereof may include those represented by the formulas (IXaa) to (IXcc):

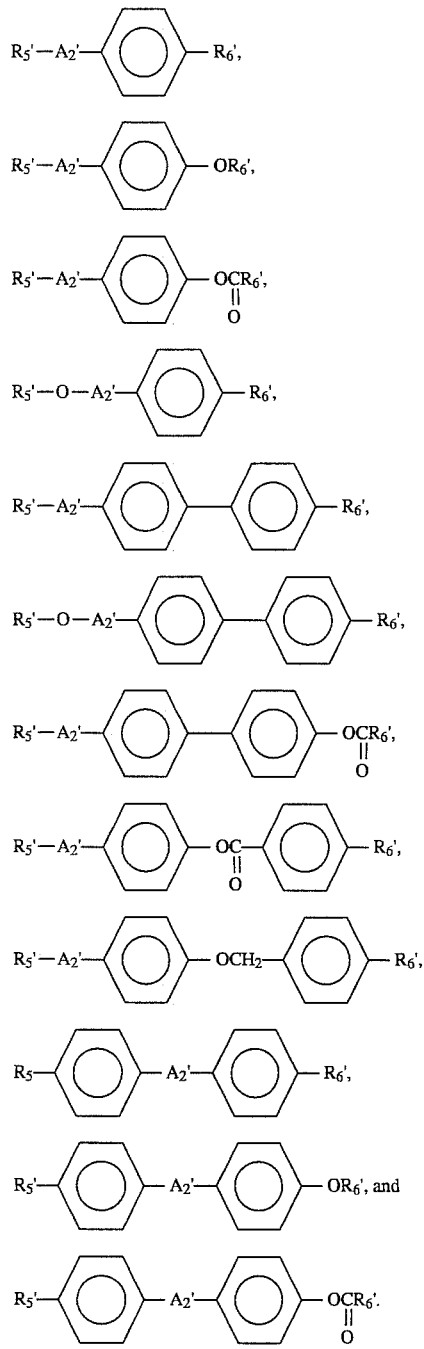

In the above-mentioned formulas (Xa) to (Xb), more preferred compounds thereof may include those represented by the formulas (Xaa) to (Xbb):

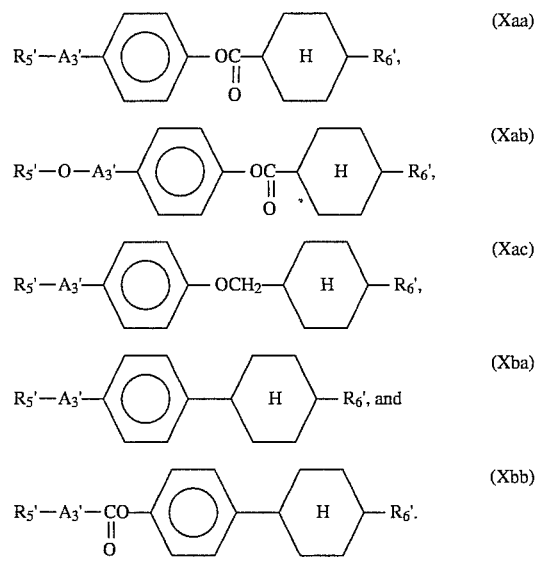

In the above formula (XI), preferred compounds thereof may include those represented by the following formulas (XIa) to (XIg):

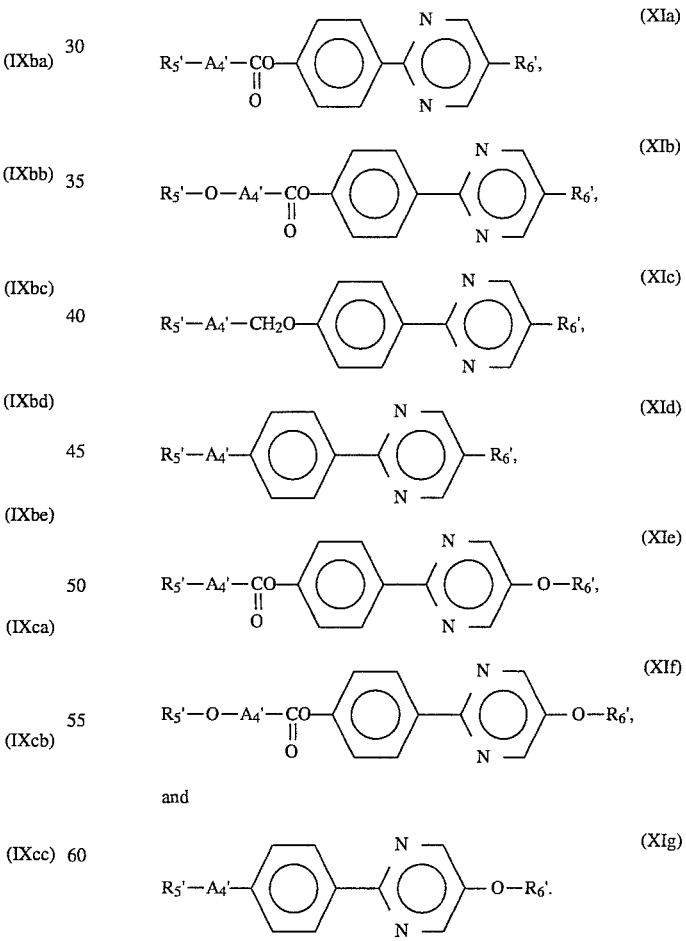

In the above-mentioned formulas (XIIa) to (XIId), more preferred compounds thereof may include those represented by the formula (XIIaa) to (XIIdb):

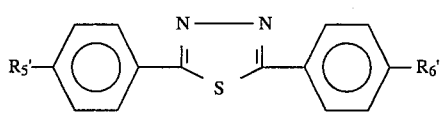 (XIIaa)

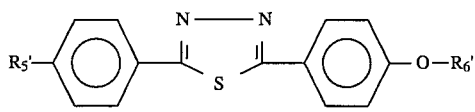 (XIIab)

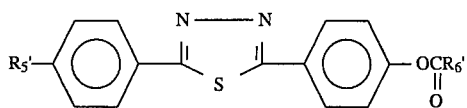 (XIIac)

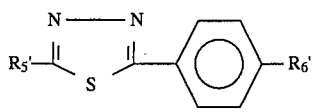 (XIIba)

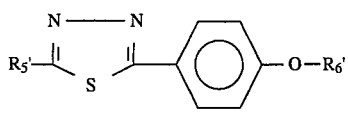 (XIIbb)

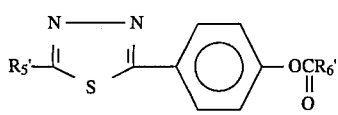 (XIIbc)

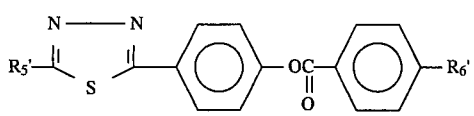 (XIIca)

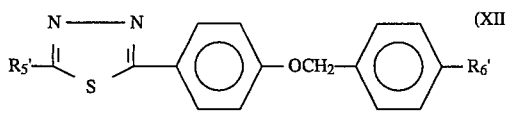 (XIIcb)

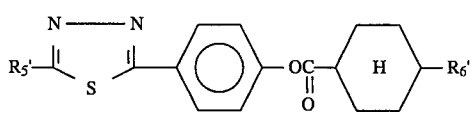 (XIIda)

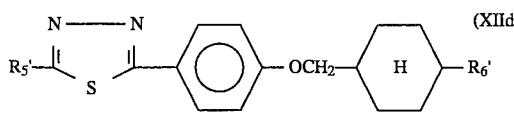 (XIIdb)

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of $$-O-, -\underset{\underset{O}{\|}}{C}-, -\underset{\underset{O}{\|}}{O C}-, -\underset{\underset{O}{\|}}{C O}-,$$

$$-\underset{\underset{CN}{|}}{C H}- \text{ and } -\underset{\underset{CN}{|}}{C C H_3}-.$$

Further, preferred examples of $R_5'$ and $R_6'$ may respectively include those represented by the following groups (i) to (vi):

i) a linear alkyl group having 1–15 carbon atoms;

ii) 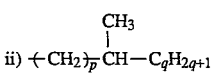

wherein p denotes an integer of 0–5 and q denotes an integer of 2–11 (optically active or inactive);

iii) 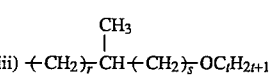

wherein r denotes an integer of 0–6, s denotes 0 or 1, and t denotes an integer of 1–14 (optically active or inactive);

iv) 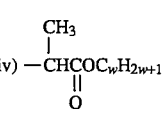

wherein w denotes an integer of 1–15 (optically active or inactive);

v) 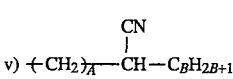

wherein A denotes an integer of 0–2 and B denotes an integer of 1–15 (optically active or inactive); and vi) 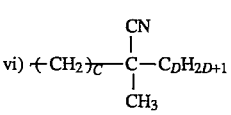

wherein C denotes an integer of 0–2 and D denotes an integer of 1–15 (optically active or inactive).

Specific examples of another mesomorphic compound may also include those represented by the following formulae (XIII) to (XVII).

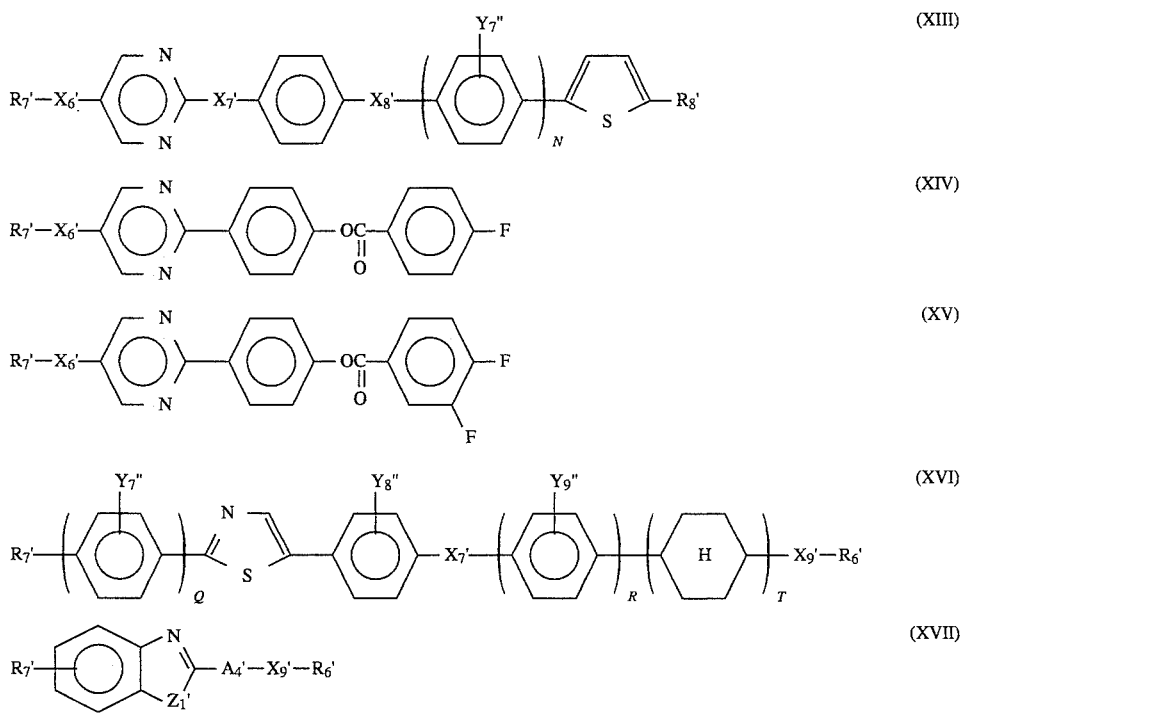

Herein, $R_7'$ and $R_8'$ respectively denote hydrogen or a linear or branched alkyl group having 1–18 carbon atoms capable of including one or non-neighboring two or more methylene groups, other than those directly connected to $X_6'$ or $X_9'$, which can be replaced with at least one species of

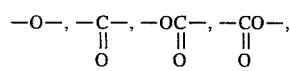

Further, preferred examples of $R_7'$ and $R_8'$ may respectively include those represented by the following groups (i) to (vii):

i) a linear alkyl group having 1–15 carbon atoms;

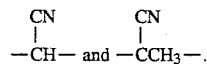

wherein p denotes an integer of 0–5 and q denotes an integer of 2–11 (optically active or inactive);

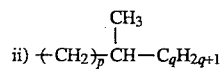

wherein r denotes an integer of 0–6, s denotes 0 or 1, and t denotes an integer of 1–14 (optically active or inactive);

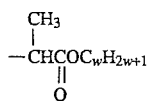

wherein w denotes an integer of 1–15 (optically active or inactive);

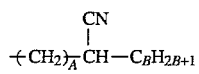

wherein A denotes an integer of 0–2 and B denotes an integer of 1–15 (optically active or inactive);

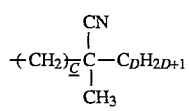

wherein C denotes an integer of 0–2 and D denotes an integer of 1–15 (optically active or inactive); and vii) H (hydrogen).

In the above formulae (XIII) to (XVII); N, Q, R and T are 0 or 1; $Y_7''$, $Y_8''$ and $Y_9''$ are H or F; $X_6'$ and $X_9'$ respectively denote a single bond, —CO—O—, —O—CO— or —O—; $X_7'$ and $X_8'$ respectively denote a single bond, —CO—O—, —O—CO—, —CH$_2$O— or —OCH$_2$—, $Z_1'$ is —O— or —S—; and $A_4'$ is

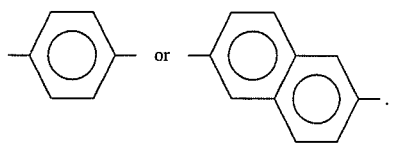

The compound of the formula (XIII) may preferably include a compound represented by the following formula (XIIIa):

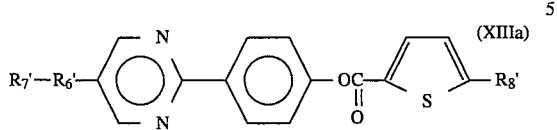

The compound of the formula (XVI) may preferably include compounds represented by the following formulae (XVIa) and (XVIb):

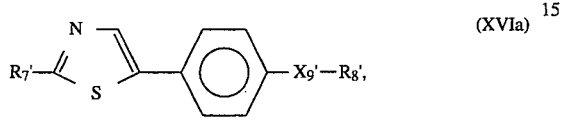

and

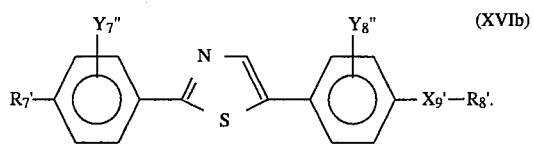

The compound of the formula (XVII) may preferably include compounds represented by the following formulae (XVIIa) to (XVIIe):

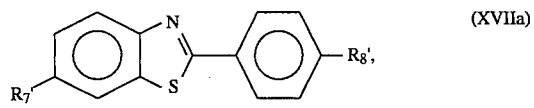

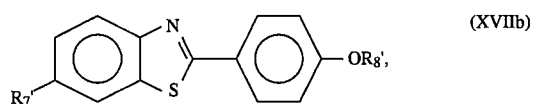

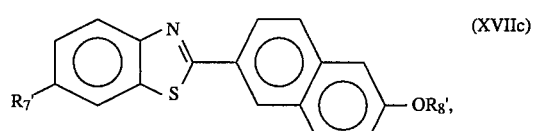

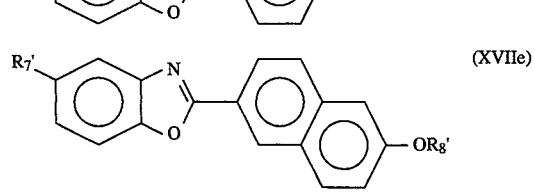

The compounds of the formulae (XVIa) and (XVIb) may preferably include compounds represented by the following formulae (XVIaa) to (XVIbc):

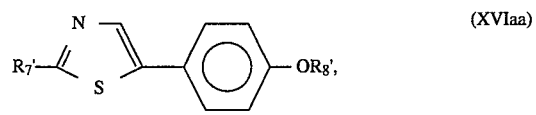

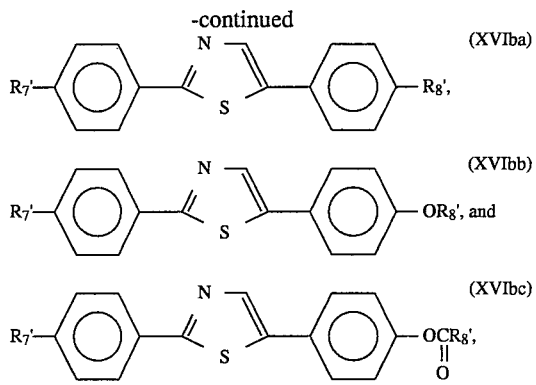

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I).

Further, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I).

The liquid crystal device according to the present invention may preferably be prepared by heating the liquid crystal composition as prepared above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity as prepared above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. In the present invention, the transparent electrode 3 may be formed oh one of the substrates 2. The glass substrates 2 are placed or arranged opposite each other. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to uniaxially align the liquid crystal molecules in the rubbing direction (uniaxial alignment treatment). Further, it is also possible to compose the alignment control layer 4 of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyesterimide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer comprising the above-mentioned inorganic material or organic insulating alignment control layer comprising the above-mentioned organic material. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, a sealing material comprising, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, a pair of polarizers 8 arranged in, e.g., right angle cross nicol relationship are applied. The device shown in FIG. 1 is of a transmission type and accordingly is provided with a light source 9 at the back of one of the polarizers 8.

Figure 2:
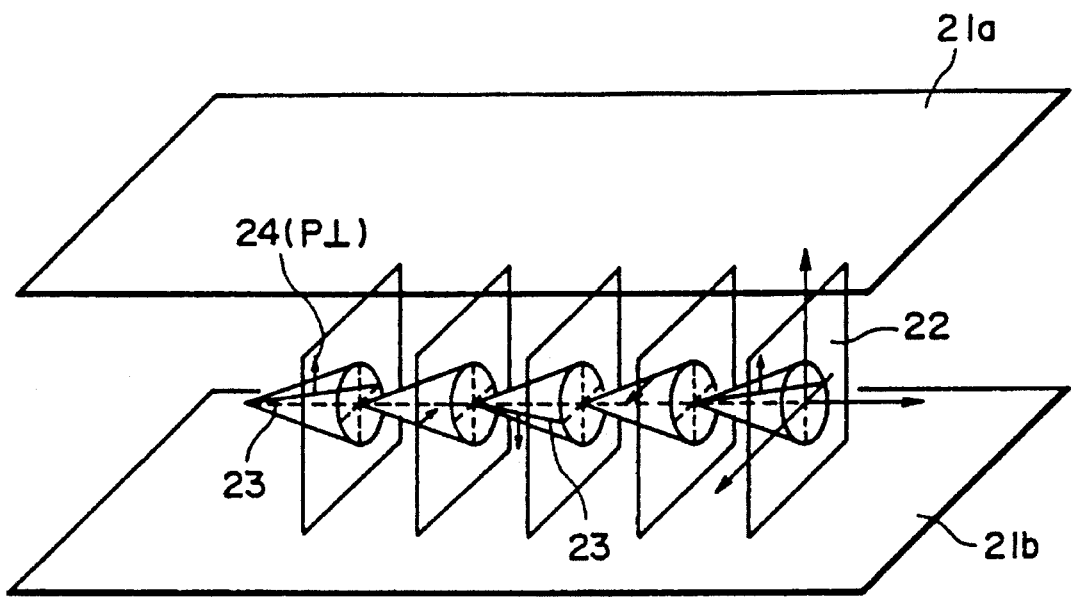
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
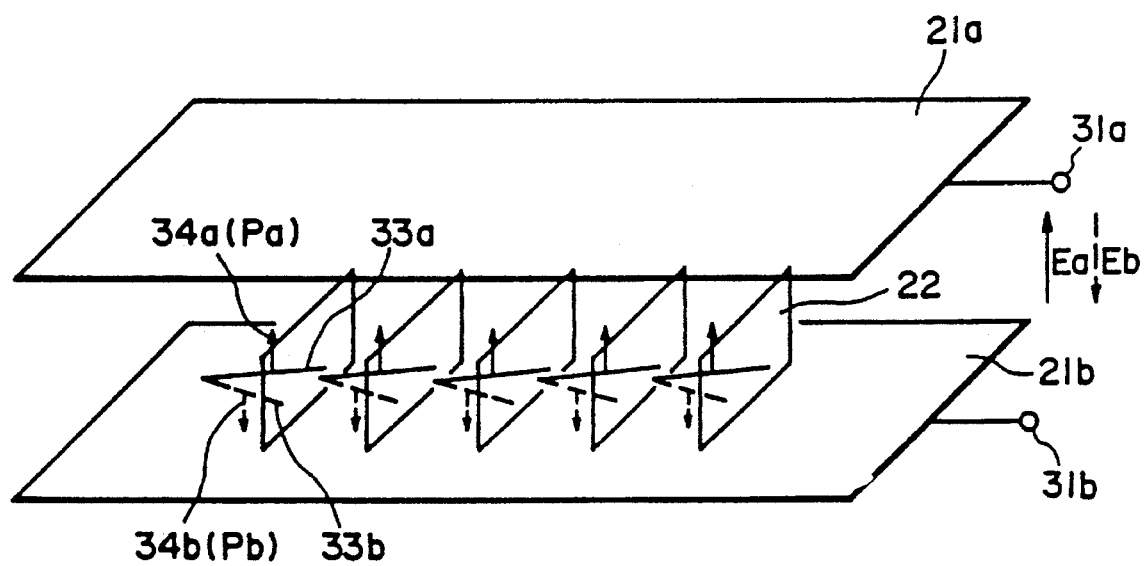

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

The liquid crystal device according to the present invention is used as an element, particularly a display element, for various liquid crystal apparatus.

Figure 4:
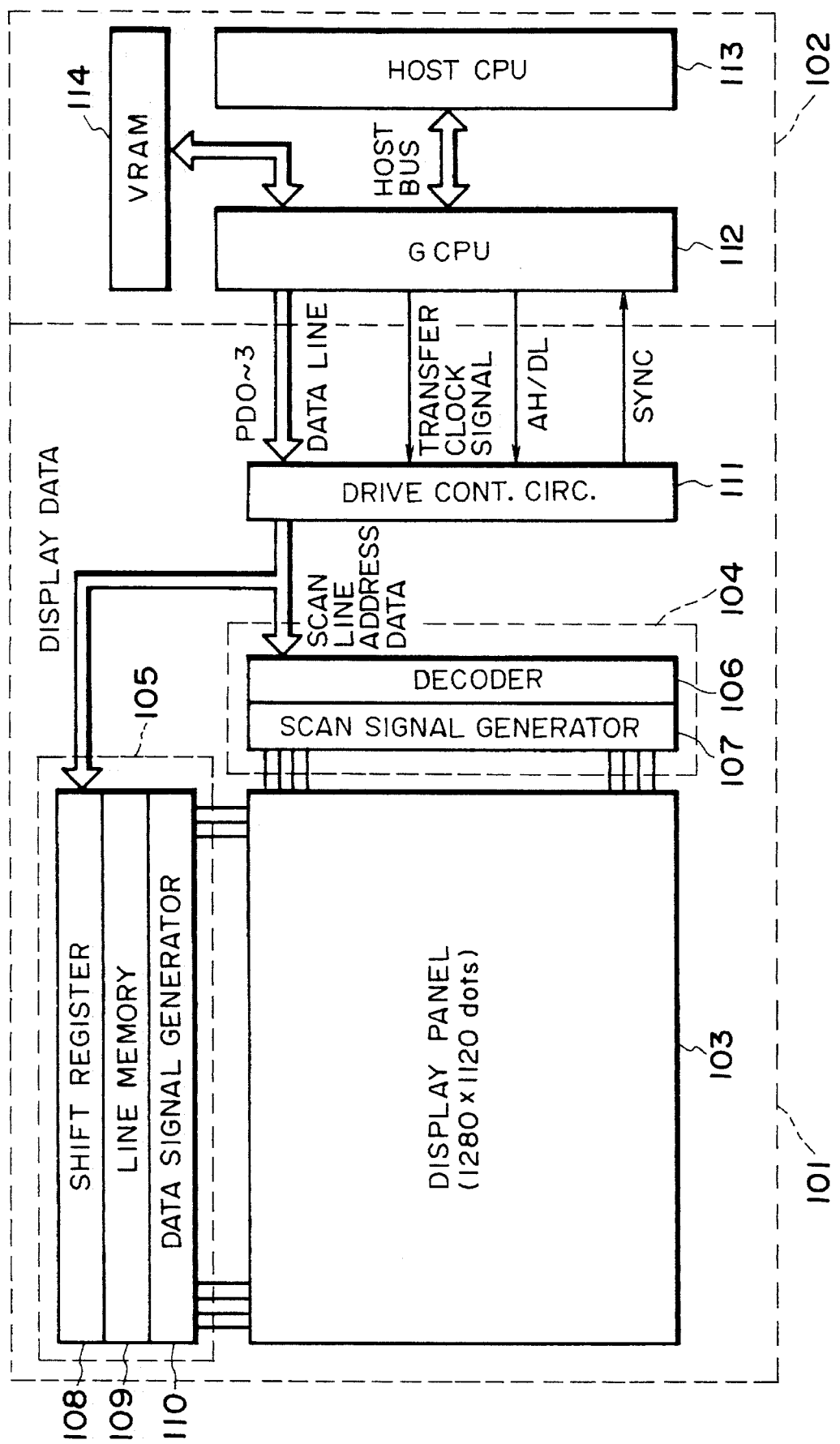
FIG. 4 is a block diagram showing a display apparatus comprising a liquid crystal device utilizing ferroelectricity of a liquid crystal composition and a graphic controller.
Figure 5:
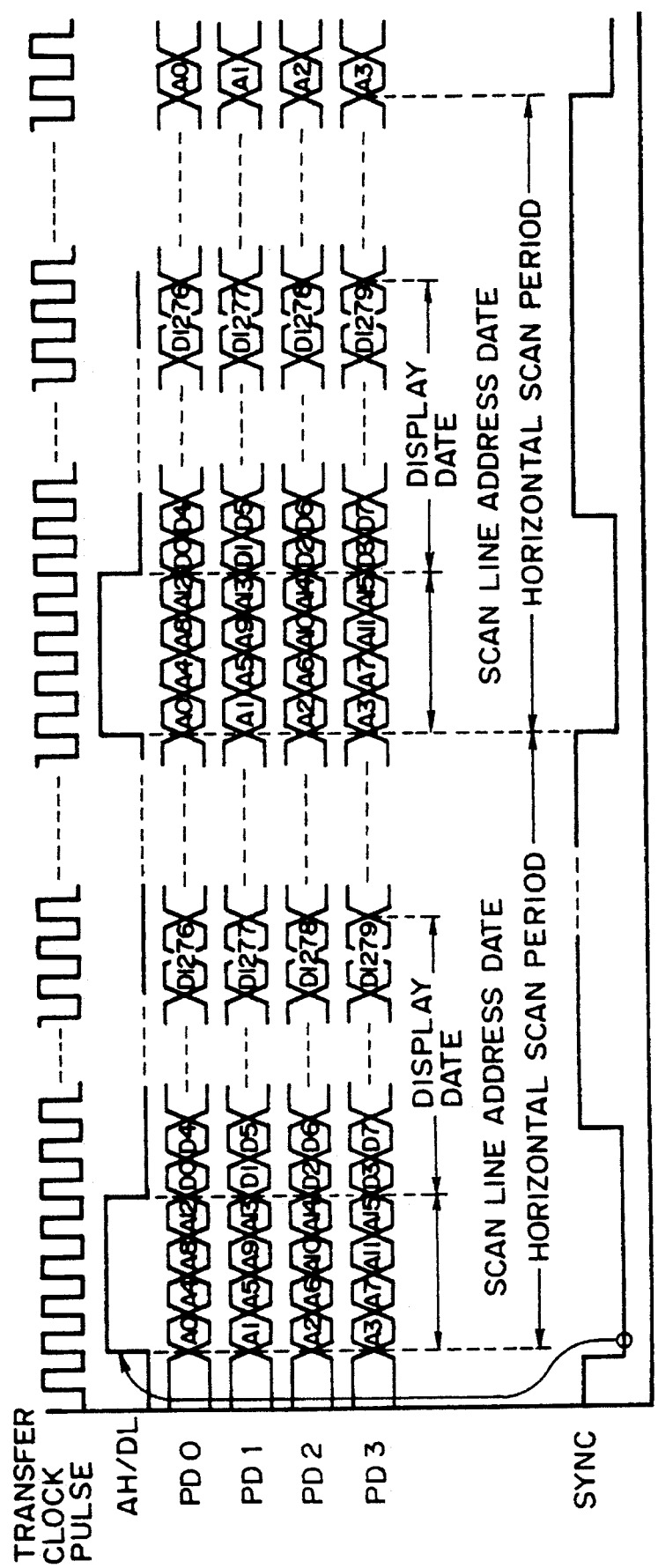
FIG. 5 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally performed by the graphic controller 102. A light source (not shown) is disposed at the back of the display panel 103.

Hereinbelow, the present invention will be explained more specifically with reference to examples. It is however to be understood that the present invention is not restricted to these examples.

EXAMPLE 1

Production of 2-(4-hexylphenyl)-5-{4-(4-cyclohexylbutyl)phenyl}thiazole (Example Compound No. (I-50))

(Step 1) Production of 4-{2-(4-hexylphenyl)thiazone-5-yl}phenyl trifluoromethylsulfonate 1.20 g of 4-{2-(4-hexylphenyl)thiazole-5-yl}phenol was dissolved in 2 ml of pyridine and cooled on an ice bath to which common salt was added. To the solution, 0.9 ml of anhydrous trifluoromethylsulfonic acid was added, followed by stirring for 1 hour. After the reaction, the reaction mixture was poured into ice water and subjected to extraction with ethyl acetate. The resultant organic layer was acidified by diluted hydrochloric acid, washed with common salt water (or brine) and dried with anhydrous sodium sulfate, followed by distilling-off of the solvent to obtain 1.66 g of an objective product.

(Step 2) Production of 2-(4-hexylphenyl)-5-{4-(4-cyclohexylbutyl)phenyl}thiadiazole 0.78 g of 4-cyclohexyl-1-butene was dissolved in 2.8 ml of tetrahydrofuran (THF) and cooled on an ice water bath to which common salt was added. At −17° C., 1.13 ml of a solution of 0.5M 9-BBN (9-borabicyclo[3,3,1]nonane) in THF was added to the solution, followed by stirring for 1 hour at −17° to −14° C. and further stirring for 2 hours at 0° to 10° C.

Then, 0.11 g of Pd (PPh$_3$)$_4$ (tetrakis(triphenylphosphine)palladium (O)) was added to the mixture. 1.66 g of 4-{2-(4-hexylphenyl)thiazole-5-yl}phenyl trifluoromethylsulfonate, 6 ml of 3M-NaOH aqueous solution and 10 ml of THF were added to the resultant mixture, followed by heat-refluxing for 2.5 hours. After the reaction, the reaction mixture was poured into water and subjected to extraction with toluene. The resultant organic layer was purified by silica gel column chromatography to obtain 0.22 g of an objective product (Yield: 13%).

EXAMPLE 2

Production of 2-(2-decylindan-5-yl)-5-(3-phenylpropyloxy)pyrimidine (Ex. Comp. No. (I-75))

0.443 g of 2-(2-decylindan-5-yl)pyrimidine-5-ol, 0.343 g of phenylpropyl p-toluenesulfonate and 0.1 g of potassium hydroxide were dissolved in 2 ml of ethanol, followed by heat-refluxing for 4 hours. After the reaction, the reaction mixture was poured into water and subjected to extraction with toluene. The resultant organic layer was washed with water and dried with anhydrous sodium sulfate, followed by distilling-off of the solvent and purification by silica gel column chromatography to obtain 0.313 g of an objective product (Yield: 53.2%).

EXAMPLE 3

Production of 2-(4-hexylphenyl)-5-{4-(4-phenylbutyloxy)phenyl}thiazole (Ex. Comp. No. (I-40))

An objective product was prepared in the same manner as in Example 2 except that 2-(2-decylindan-5-yl)pyrimidine-5-ol was changed to 4-{2-(4-hexylphenyl)thiazole-5-yl}phenol and 3-phenylpropyl p-toluenesulfonate was changed to 4-phenylbutyl p-toluenesulfonate (Yield: 71.1%).

EXAMPLE 4

Production of 2-{4-(3-cyclohexylpropyloxy)phenyl}-6-octylbenzothiazole (Ex. Comp. No. (I-8))

An objective product was prepared in the same manner as in Example 2 except that 2-(2-decylindan-5-yl)pyrimidine-5-ol was changed to 4-(6-octylbenzothiazole-2-yl)phenol and 3-phenylpropyl p-toluenesulfonate was changed to 3-cyclohexylpropyl p-toluenesulfonate (Yield: 56.4%).

EXAMPLE 5

Production of 2-{4-(5-cyclohexylpentyloxy)phenyl}-6-octylbenzothiazole (Ex. Comp. No. (I-10))

An objective product was prepared in the same manner as in Example 2 except that 2-(2-decylindan-5-yl)pyrimidine-5-ol was changed to 4-(6-octylbenzothiazole-2-yl)phenol and 3-phenylpropyl p-toluenesulfonate was changed to 5-cyclohexylpentyl p-toluenesulfonate (Yield: 62.4%).

EXAMPLE 6

Production of 5-{4-(3-cyclohexylpropyloxy)phenyl}-2-decylthiazole (Ex. Comp. No. (I-61))

An objective product was prepared in the same manner as in Example 2 except that 2-(2-decylindan-5-yl)pyrimidine-5-ol was changed to 4-(5-decylthiazole-2-yl)phenol and 3-phenylpropyl p-toluenesulfonate was changed to 3-cyclohexylpropyl p-toluenesulfonate (Yield: 25.6%).

EXAMPLE 7

Production of 2-(4-pentylphenyl)-6-(5-phenylpentyloxy)quinoline (Ex. Comp. No. (I-91))

An objective product was prepared in the same manner as in Example 2 except that 2-(2-decylindan-5-yl)pyrimidine-5-ol was changed to 2-(4-pentylphenyl)quinoline-6-ol and 3-phenylpropyl p-toluenesulfonate was changed to 5-phenylpentyl p-toluenesulfonate (Yield: 58.3%).

EXAMPLE 8

Production of 4-{2-(4-hexylphenyl)thiazole-5-yl}phenyl 4-phenyl-1-butanoate (Ex. Comp. No. (I-41))

0.675 g of 4-{2-(4-hexylphenyl)thiazole-5-yl}phenol, 0.328 g of 4-phenylbutanoic acid, 0.41 g of DCC (1,3-dicyclohexylcarbodiimide) and 40 mg of 4-(N-pyrrolidino)pyridine were dissolved in 40 ml of dichloromethane, followed by stirring overnight. After the reaction, the reaction was subjected to filtration to remove an insoluble matter, followed by distilling-off of the solvent and purification by silica gel column chromatography to obtain 0.260 g of an objective product (Yield: 26.9%).

EXAMPLE 9

Production of 3-phenylpropyl 4-(5-butylbenzoxazole-2-yl)benzoate (Ex. Comp. No. (I-34))

An objective product was prepared in the same manner as in Example 8 except that 4-{2-(4-hexylphenyl)thiazole-5-yl}phenol was changed to 3-phenylpropanol and 4-phenylbutanoic acid was changed to 4-(5-butylbenzoxazole-2-yl)benzoic acid (Yield: 26.3%).

EXAMPLE 10

Production of 4-{2-(4-hexylphenyl)thiazole-5-yl}phenyl 5-cyclohexylpentanoate (Ex. Comp. No. (I-52))

An objective product was prepared in the same manner as in Example 8 except that 4-phenylbutanoic acid was changed to 5-cyclohexylpentanoic acid (Yield: 53.0%).

EXAMPLE 11

Production of 4-(5-decylpyrimidine-2-yl)phenyl 5-(1,2-dithiolan-3-yl)pentanoate (Ex. Comp. No. (I-67))

An objective product was prepared in the same manner as in Example 8 except that 4-{2-(4-hexylphenyl)thiazole-5-yl}phenol was changed to 4-(5-decylpyrimidine-2-yl)phenol and 4-phenylbutanoic acid was changed to (1,2-dithiolan-3-yl)pentanoic acid (Yield: 83.0%).

EXAMPLE 12

Production of 4-{2-(4-hexylphenyl)thiazole-5-yl}phenyl 5-(4-butylcyclohexyl)pentanoate (Ex. Comp. No. (I-133))

An objective product was prepared in the same manner as in Example 8 except that 4-phenylbutanoic acid was changed to 5-(4-butylcyclohexyl)pentanoic acid (Yield: 83.1%).

The mesomorphic compounds prepared in Examples 1–12 showed the following phase transition series.

| Ex. No. | Ex. Comp. No. | Phase transition temperature (°C.) |
|---|---|---|
| 1 | (I-50) | Cryst $\underset{76}{\overset{87}{\rightleftarrows}}$ SmC $\underset{100}{\overset{100}{\rightleftarrows}}$ SmA $\underset{123}{\overset{124}{\rightleftarrows}}$ N $\underset{125}{\overset{125}{\rightleftarrows}}$ Iso |
| 2 | (I-75) | Cryst $\overset{87}{\rightarrow}$ Iso; $\underset{76}{\nwarrow}$ Sm3 $\underset{77}{\swarrow}$ |
| 3 | (I-40) | Cryst $\overset{73}{\rightarrow}$ SmC $\underset{78}{\overset{79}{\rightleftarrows}}$ SmA $\underset{85}{\overset{86}{\rightleftarrows}}$ N $\underset{94}{\overset{94}{\rightleftarrows}}$ Iso; $\underset{<0}{\nwarrow}$ Sm3 $\underset{48}{\swarrow}$ |
| 4 | (I-8) | Cryst $\overset{92}{\rightarrow}$ SmC $\underset{97}{\overset{98}{\rightleftarrows}}$ N $\underset{103}{\overset{105}{\rightleftarrows}}$ Iso; $\underset{<-20}{\nwarrow}$ Sm4 $\underset{56}{\leftarrow}$ Sm3 $\underset{68}{\swarrow}$ |
| 5 | (I-9) | Cryst $\underset{74}{\overset{99}{\rightleftarrows}}$ SmC $\underset{105}{\overset{106}{\rightleftarrows}}$ Iso |
| 6 | (I-61) | Cryst $\overset{84}{\rightarrow}$ Iso; $\underset{61}{\nwarrow}$ Sm3 $\underset{63}{\swarrow}$ |
| 7 | (I-91) | Cryst $\overset{111}{\rightarrow}$ Iso; $\underset{68}{\nwarrow}$ SmA $\underset{110}{\swarrow}$ |
| 8 | (I-41) | Cryst $\underset{76}{\overset{79}{\rightleftarrows}}$ SmC $\underset{96}{\overset{97}{\rightleftarrows}}$ N $\underset{98}{\overset{100}{\rightleftarrows}}$ Iso |

-continued

| Ex. No. | Ex. Comp. No. | Phase transition temperature (°C.) |
|---|---|---|
| 9 | (I-34) | Cryst $\underset{65}{\overset{89}{\rightleftarrows}}$ Iso |
| 10 | (I-52) | Cryst $\overset{92}{\longrightarrow}$ SmC $\underset{133}{\overset{134}{\rightleftarrows}}$ N $\underset{143}{\overset{143}{\rightleftarrows}}$ Iso<br><0 Sm5 $\underset{61}{\longleftarrow}$ Sm4 $\underset{63}{\longleftarrow}$ Sm3 $\longleftarrow$ 70 |
| 11 | (I-67) | Cryst $\underset{52}{\overset{64}{\rightleftarrows}}$ Iso |
| 12 | (I-133) | Cryst $\underset{111}{\overset{112}{\rightleftarrows}}$ SmC $\underset{153}{\overset{153}{\rightleftarrows}}$ SmA $\underset{191}{\overset{191}{\rightleftarrows}}$ N $\underset{192}{\overset{193}{\rightleftarrows}}$ Iso |

Herein, the respective symbols denote the following phases; Iso: isotropic phase; N: nematic phase; SmA: smectic A phase; SmC: smectic C phase; SmC*: chiral smectic C phase; Sm3, Sm4 and Sm5: smectic phase other than SmA and SmC; and Cryst.: crystal.

EXAMPLE 13

A liquid crystal composition A was prepared by mixing the following compounds in the indicated proportions.

Hereinbelow, the respective abbreviations denote the following cyclic groups.

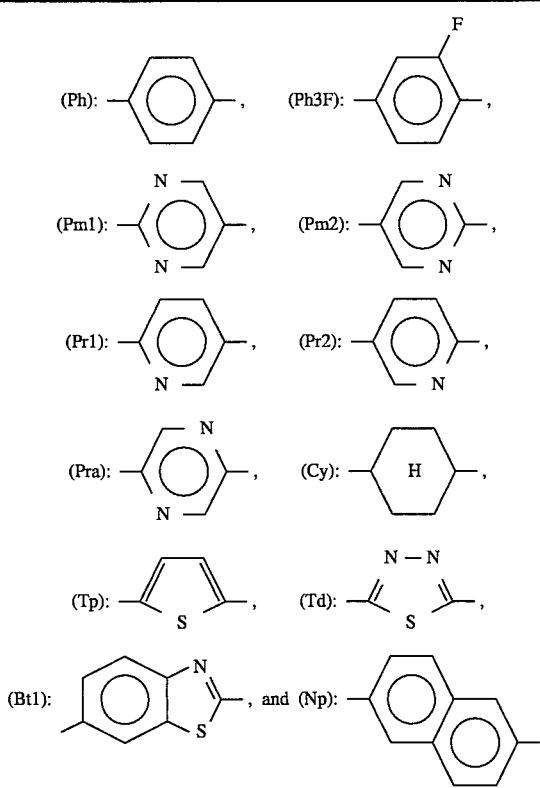

| Structural formula | wt. parts |
|---|---|
| $C_6H_{13}$ — (Pm2) — (Ph) — $OC_{12}H_{25}$ | 4.0 |
| $C_8H_{17}$ — (Pm2) — (Ph) — $OC_9H_{19}$ | 8.0 |
| $C_8H_{17}$ — (Pm2) — (Ph) — $OC_{10}H_{21}$ | 8.0 |
| $C_9H_{19}$ — (Pm2) — (Ph) — $OC_8H_{17}$ | 4.0 |
| $C_{10}H_{21}O$ — (Ph) — COO — (Ph) — $OCH_2CH(CH_3)C_2H_5$ | 26.0 |
| $C_6H_{13}$ — (Bt1) — (Ph) — $OC_8H_{17}$ | 20.0 |
| $C_5H_{11}$ — (Ph) — (Td) — (Ph) — $C_5H_{11}$ | 2.5 |
| $C_6H_{13}$ — (Ph) — (Td) — (Ph) — $C_4H_9$ | 2.5 |
| $C_{11}H_{23}$ — (Pm2) — (Ph) — OCO — (Tp) — $C_4H_9$ | 3.3 |
| $C_{11}H_{23}$ — (Pm2) — (Ph3F) — OCO — (Tp) — $C_4H_9$ | 1.7 |
| $C_{10}H_{21}$ — (Pm2) — (Ph) — $OC_2C^*H(F)C_6H_{13}$ | 10.0 |

The liquid crystal composition A was further mixed with the following example compound (I-40) prepared in Example 3 in the indicated proportions to provide a liquid crystal composition B.

| Ex. Comp. No. | wt. parts |
|---|---|
| (I-40) | 10 |
| Composition A | 90 |

The liquid crystal composition B showed the following phase transition series.

Phase transition temperature (°C.)

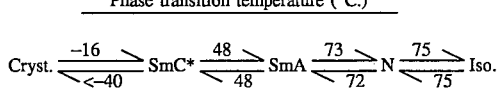

EXAMPLE 14

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth to effect uniaxial alignment treatment. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition B prepared in Example 13 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

The ferroelectric liquid crystal device was subjected to measurement of the magnitude of spontaneous polarization (Ps) and an optical response time (time from voltage application until the transmittance change reaches 90% of the maximum under the application of a peak-to-peak voltage Vpp of 20 V in combination with right-angle cross-nicol polarizers). The results are shown below.

|  | 10° C. | 30° C. | 40° C. |
|---|---|---|---|
| Response time (μsec) | 253 | 92 | 28 |
| Ps (nC/cm$^2$) | 10.0 | 7.1 | 2.6 |

EXAMPLE 15

A liquid crystal composition C was prepared by mixing the following compounds in the indicated proportions.

| Structural formula | wt. parts |
|---|---|
| $C_6H_{13}$-(Pm2)-(Ph)-$OC_{12}H_{25}$ | 2.3 |
| $C_8H_{17}$-(Pm2)-(Ph)-$OC_9H_{19}$ | 4.7 |
| $C_8H_{17}$-(Pm2)-(Ph)-$OC_{10}H_{21}$ | 4.7 |
| $C_9H_{19}$-(Pm2)-(Ph)-$OC_8H_{17}$ | 2.3 |
| $C_{10}H_{21}$O-(Ph)-COO-(Ph)-$OCH_2CH(CH_3)C_2H_5$ | 26.0 |
| $C_6H_{13}$-(Btl)-(Ph)-$OC_8H_{17}$ | 20.0 |
| $C_5H_{11}$-(Ph)-(Td)-(Ph)-$C_5H_{11}$ | 5.0 |
| $C_6H_{13}$-(Ph)-(Td)-(Ph)-$C_4H_9$ | 5.0 |
| $C_{11}H_{23}$-(Pm2)-(Ph)-OCO-(Tp)-$C_4H_9$ | 6.7 |
| $C_{11}H_{23}$-(Pm2)-(Ph3F)-OCO-(Tp)-$C_4H_9$ | 3.3 |
| $C_{10}H_{21}$-(Pm2)-(Ph)-$OCH_2C^*H(F)C_6H_{13}$ | 10.0 |

The liquid crystal composition C was further mixed with the following example compound (I-75) prepared in Example 2 in the indicated proportions to provide a liquid crystal composition D.

| Ex. Comp. No. | wt. parts |
|---|---|
| (I-75) | 10 |
| Composition C | 90 |

The liquid crystal composition D showed the following phase transition series.

Phase transition temperature (°C.)

$$\text{Cryst.} \xrightleftharpoons[<-40]{<-40} \text{SmC*} \xrightleftharpoons[51]{51} \text{SmA} \xrightleftharpoons[75]{75} \text{N} \xrightleftharpoons[82]{82} \text{Iso.}$$

EXAMPLE 16

A ferroelectric liquid crystal device was prepared in the same manner as in Example 14 except that the above liquid crystal composition D was used, and the device was subjected to measurement of Ps and response time. The results of the measurement are shown below.

|  | 10° C. | 30° C. | 45° C. |
|---|---|---|---|
| Response time (μsec) | 203 | 75 | 30 |
| Ps (nC/cm$^2$) | 10.7 | 8.3 | 3.8 |

EXAMPLE 17

A liquid crystal composition E was prepared by mixing the following compounds in the indicated proportions.

| Structural formula | wt.parts |
|---|---|
| $C_6H_{13}$-(Pm2)-(Ph)-$OC_{12}H_{25}$ | 4.0 |
| $C_8H_{17}$-(Pm2)-(Ph)-$OC_9H_{19}$ | 8.0 |
| $C_8H_{17}$-(Pm2)-(Ph)-$OC_{10}H_{21}$ | 8.0 |
| $C_9H_{19}$-(Pm2)-(Ph)-$OC_8H_{17}$ | 4.0 |
| $C_{10}H_{21}$O-(Ph)-COO-(Ph)-$OCH_2CH(CH_3)C_2H_5$ | 16.0 |
| $C_6H_{13}$-(Btl)-(Ph)-$OC_8H_{17}$ | 20.0 |
| $C_5H_{11}$-(Ph)-(Td)-(Ph)-$C_5H_{11}$ | 5.0 |
| $C_6H_{13}$-(Ph)-(Td)-(Ph)-$C_4H_9$ | 5.0 |
| $C_{11}H_{23}$-(Pm2)-(Ph)-OCO-(Tp)-$C_4H_9$ | 6.7 |
| $C_{11}H_{23}$-(Pm2)-(Ph3F)-OCO-(Tp)-$C_4H_9$ | 3.3 |
| $C_{10}H_{21}$-(Pm2)-(Ph)-$OCH_2C^*H(F)C_6H_{13}$ | 10.0 |

The liquid crystal composition E was further mixed with the following example compound (I-67) prepared in Example 11 in the indicated proportions to provide a liquid crystal composition F.

| Ex. Comp. No. | wt. parts |
|---|---|
| (I-67) | 10 |
| Composition E | 90 |

The liquid crystal composition F showed the following phase transition series.

Phase transition temperature (°C.)

$$\text{Cryst.} \xrightleftharpoons[-32]{-13} \text{SmC*} \xrightleftharpoons[48]{48} \text{SmA} \xrightleftharpoons[68]{68} \text{N} \xrightleftharpoons[75]{75} \text{Iso.}$$

EXAMPLE 18

A ferroelectric liquid crystal device was prepared in the same manner as in Example 14 except that the above liquid crystal composition F was used, and the device was subjected to measurement of Ps and response time. The results of the measurement are shown below.

|  | 10° C. | 30° C. | 45° C. |
|---|---|---|---|
| Response time (μsec) | 195 | 97 | 27 |
| Ps (nC/cm$^2$) | 9.6 | 6.8 | 2.1 |

EXAMPLE 19

A liquid crystal composition G was prepared by mixing the following compounds in the indicated proportions.

| Structural formula | wt. parts |
|---|---|
| $C_7H_{15}$-(Pm2)-(Ph)-$OC_9H_{19}$ | 12 |
| $C_{11}H_{23}$-(Pm2)-(Ph)-$OC_6H_{13}$ | 10 |
| $C_8H_{17}$-(Pm2)-(Ph)-O-$(CH_2)_5$-$C^*H(CH_3)C_2H_5$ | 10 |
| $C_{10}H_{21}$-(Pm2)-(Ph)-O-$(CH_2)_4$-$C^*H(CH_3)OCH_3$ | 3 |
| $C_8H_{17}$-(Pm2)-(Ph)-(Ph)-$OC_6H_{13}$ | 8 |
| $C_6H_{13}$O-(Ph)-OCO-(Np)-$OC_9H_{19}$ | 4 |
| $C_3H_7$-(Cy)-COO-(Ph)-(Pm1)-$C_{11}H_{23}$ | 6 |
| $C_8H_{17}$-(Cy)-COO-(Ph)-(Pm1)-$C_{11}H_{23}$ | 2 |
| $C_5H_{11}$-(Cy)-COO-(Ph)-(Pm1)-$C_{11}H_{23}$ | 8 |
| $C_{10}H_{21}$O-(Ph)-COO-(Ph)-$OCH_2C^*H(CH_3)C_2H_5$ | 15 |
| $C_4H_9$-(Cy)-$CH_2$O-(Ph)-(Pm1)-$C_6H_{13}$ | 7 |
| $C_5H_{11}$-(Cy)-$CH_2$O-(Ph)-(Pm1)-$C_6H_{13}$ | 7 |
| $C_9H_{19}$O-(Ph)-$OCH_2$-(Ph)-(Ph)-$C_7H_{15}$ | 4 |
| $C_6H_{13}C^*H(CH_3)$O-(Ph)-COO-(Ph)-(Ph)-$OCOC^*H(CH_3)OC_4H_9$ | 2 |
| $C_{12}H_{25}$-(Pm2)-(Ph)-$OCOC^*H(Cl)C^*H(CH_3)C_2H_5$ | 2 |

The liquid crystal composition G was further mixed with the following example compounds in the indicated proportions to provide a liquid crystal composition H

| Ex. Comp. No. | wt. parts |
|---|---|
| (I-134) | 2 |
| (I-21) | 3 |
| (I-86) | 2 |
| Composition G | 93 |

A ferroelectric liquid crystal device was prepared in the same manner as in Example 14 except that the above liquid crystal composition H was used, and the device was subjected to measurement of response time. The results of the measurement are shown below.

|  | 10° C. | 25° C. | 40° C. |
|---|---|---|---|
| Response time (μsec) | 784 | 373 | 197 |

COMPARATIVE EXAMPLE 1

A ferroelectric liquid crystal device was prepared and subjected to measurement of response time in the same manner as in Example 19 except for injecting the composition G alone into a blank cell, whereby the following results were obtained.

|  | 10° C. | 25° C. | 40° C. |
|---|---|---|---|
| Response time (μsec) | 784 | 373 | 197 |

EXAMPLE 20

A liquid crystal composition J was prepared by mixing the following Example Compounds instead of those of (I-134), (I-21) and (I-86) used in Example 19 in the indicated proportions with the liquid crystal composition G.

| Ex. Comp. No. | wt. parts |
|---|---|
| (I-48) | 4 |
| (I-60) | 2 |
| (I-38) | 1 |
| Composition G | 95 |

A ferroelectric liquid crystal device was prepared in the same manner as in Example 14 except that the above liquid crystal composition J was used, and the device was subjected to measurement of response time. The results of the measurement are shown below.

|  | 10° C. | 25° C. | 45° C. |
|---|---|---|---|
| Response time (μsec) | 610 | 324 | 180 |

EXAMPLE 21

A liquid crystal composition K was prepared by mixing the following compounds in the indicated proportions.

| Structural formula | wt. parts |
|---|---|
| $C_9H_{19}$-(Pm2)-(Ph)-$OC_9H_{19}$ | 6 |
| $C_{10}H_{21}$-(Pm2)-(Ph)-$OC_8H_{17}$ | 6 |
| $C_8H_{17}$O-(Pr1)-(Ph)-O-$(CH_2)_5$-$C^*H(CH_3)C_2H_5$ | 7 |
| $C_{11}H_{23}$-(Pm2)-(Ph)-O-$(CH_2)_2$-$C^*H(CH_3)C_2H_5$ | 14 |
| $C_{10}H_{21}$-(Pr2)-(Ph)-$C_6H_{13}$ | 8 |
| $C_6H_{13}$-(Pm2)-(Ph)-(Ph)-$C_4H_9$ | 4 |
| $C_8H_{17}$-(Ph)-(Pr2)-(Ph)-$OC_5H_{11}$ | 2 |
| $C_3H_7$-(Cy)-COO-(Ph)-(Pm1)-$C_{12}H_{25}$ | 10 |
| $C_5H_{11}$-(Cy)-COO-(Ph)-(Pm1)-$C_{12}H_{25}$ | 5 |
| $C_{10}H_{21}$O-(Ph)-COS-(Ph)-$OC_8H_{17}$ | 10 |
| $C_6H_{13}$-(Ph)-COO-(Ph)-(Ph)-$OCH_2CH(CH_3)C_2H_5$ | 7 |
| $C_3H_7$-(Cy)-$CH_2$O-(Ph)-(Pm1)-$C_8H_{17}$ | 7 |
| $C_{10}H_{21}$-(Ph)-(Ph)-$OCH_2$-(Ph)-$C_7H_{15}$ | 5 |
| $C_{12}H_{25}$-(Pm2)-(Ph)-$OCH_2C^*H(F)C_5H_{11}$ | 2 |
| $C_5H_{11}$-(Cy)-COO(Ph)-$OCH_2C^*H(F)C_6H_{13}$ | 2 |
| $C_{12}H_{25}$O-(Ph)-(Pra)-COO-$(CH_2)_3$-$CH(CH_3)C_2H_5$ | 2 |
| $C_{12}H_{25}$O-(Ph)-(Pra)-O-$(CH_2)_3$-$CH(CH_3)OC_3H_7$ | 3 |

The liquid crystal composition K was further mixed with the following compounds in the proportions indicated below to provide a liquid crystal composition L.

| Ex. Comp. No. | wt. parts |
|---|---|
| (I-81) | 3 |
| (I-126) | 1 |
| (I-135) | 3 |
| Composition K | 93 |

A ferroelectric liquid crystal device was prepared in the same manner as in Example 14 except that the above liquid crystal composition L was used, and the device was subjected to measurement of optical response time and observation of switching states. In the device, a monodomain with a good and uniform alignment characteristic was observed. The results are shown below.

| | 10° C. | 25° C. | 40° C. |
|---|---|---|---|
| Response time (μsec) | 475 | 269 | 158 |

COMPARATIVE EXAMPLE 2

A ferroelectric liquid crystal device was prepared and subjected to measurement of response time in the same manner as in Example 14 except for injecting the composition K alone used in Example 21 into a blank cell, whereby the following results were obtained.

| | 10° C. | 25° C. | 40° C. |
|---|---|---|---|
| Response time (μsec) | 668 | 340 | 182 |

As apparent from the above Examples 19 to 21 and Comparative Examples 1 and 2, the ferroelectric liquid crystal device including the liquid crystal compositions H, J and L, i.e., compositions containing a mesomorphic compound of the formula (I) according to the present invention, provided improved operation characteristic at a lower temperature, high speed responsiveness and a decreased temperature dependence of response speed.

EXAMPLE 22

A blank cell was prepared in the same manner as in Example 14 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition L used in Example 21. The liquid crystal device was subjected to measurement response time in the same manner as in Example 14. The results are shown below.

| | 10° C. | 25° C. | 40° C. |
|---|---|---|---|
| Response time (μsec) | 496 | 276 | 160 |

EXAMPLE 23

A blank cell was prepared in the same manner as in Example 14 except for omitting the $SiO_2$ layer to form an alignment control layer composed of the polyimide resin layer alone on each electrode plate. A ferroelectric liquid crystal devices were prepared by filling such a blank cell with liquid crystal composition L used in Example 21. The liquid crystal device was subjected to measurement of response time in the same manner as in Example 14. The results are shown below.

| | 10° C. | 25° C. | 40° C. |
|---|---|---|---|
| Response time (μsec) | 486 | 268 | 152 |

As is apparent from the above Examples 22 and 23, also in the case of a different device structure, the device containing the ferroelectric liquid crystal composition L according to the present invention provided an improved low-temperature operation characteristic and a decreased temperature dependence of response speed similarly as in Example 21.

As described hereinabove, according to the present invention, by utilizing a ferroelectricity exhibited by a liquid crystal composition containing at least one mesomorphic compound of the formula (I), there is provided a liquid crystal device providing improved characteristic such as a good alignment characteristic, a good switching property, high-speed responsiveness, a decreased temperature-dependence of response speed, and an improved low-temperature operation characteristic.

In addition, when the liquid crystal device is used as a display device in combination with a light source, drive circuit, etc., a liquid crystal apparatus, such as a liquid crystal display apparatus, providing good display characteristics can be realized.

What is claimed is:

1. A mesomorphic compound represented by the following formula (I):

$$R^1\text{---}A\text{---}R^2 \qquad (I),$$

wherein $R^1$ and $R^2$ independently denote $R^3$ or $R^4\text{---}A^0\text{---}Y^1\text{---}(CH_2)_m Y^2\text{---}$, and at least one of $R^1$ and $R^2$ is $R^4\text{---}A^0\text{---}Y^1\text{---}(CH_2)_m Y^2\text{---}$, in which $R^3$ denotes H, F, or a linear, branched or cyclized alkyl group having 1–18 carbon atoms capable of including at least one —$CH_2$— group which can be replaced with —O—, —S—, —CO—, —CH=CH—, —C≡C— or —CH(CN)— provided that heteroatoms are not adjacent to each other and capable of including at least one H which can be replaced with F, $R^4$ denotes H, F or a linear or branched alkyl group having 1–12 carbon atoms capable of including at least one —$CH_2$— group which can be replaced with —O—, —S—, —CO—, —CH=CH—, —C≡C— or —CH(CN)— provided that heteroatoms are not adjacent to each other and capable of including at least one H which can be replaced with F, $Y^1$ and $Y^2$ independently denote —$CH_2$—, —O—, —COO— or —OCO—, and m is an integer of 1–16; and A denotes —$A^1$—Z—$A^2$— or —$A^1$—$A^2$—Z—$A^3$— in which Z denotes a single bond, —$CH_2$—, —$OCH_2$—, —COO—, —OCO—, —COS—, —SCO—, —C≡C— or —CH=CH—, and $A^0$, $A^1$, $A^2$ and $A^3$ independently denote a divalent cyclic group selected from α class or β class listed below, and at least one of $A^0$, $A^1$, $A^2$ and $A^3$ independently denotes a divalent cyclic group selected from the β class, α class: 1,4-phenylene capable of including at least one H which can be replaced with. F, $CH_3$ or $CF_3$; 1,4-cyclohexylene; pyrimidine-2,5-diyl; pyridine-2,5-diyl; thiazole-2,5-diyl; thiophene-2,5-diyl; and 2,6-naphthylene, and β class: thiazole-2,5-diyl; benzothiazole-2,6-diyl; benzoxazole-2,5-diyl; indan-2,5-diyl; coumaran-2,5-diyl; quinoxaline-2,6-diyl; quinoline-2,6-diyl; 1,2-dithiolan-3,5-diyl; and furan-2,5-diyl.

2. A compound according to claim 1, which is represented by any one of the following formulae (Ia) to (Ig):

$$R^1-A\text{+}CH_2\text{)}_{\overline{m+2}}-A^0-R^4, \quad \text{(Ia)}$$

$$R^1-A-O\text{+}CH_2\text{)}_{\overline{m+1}}-A^0-R^4, \quad \text{(Ib)}$$

$$R^1-A-OCO\text{+}CH_2\text{)}_{\overline{m+1}}-A^0-R^4, \quad \text{(Ic)}$$

$$R^1-A-COO\text{+}CH_2\text{)}_{\overline{m+1}}-A^0-R^4, \quad \text{(Id)}$$

$$R^1-A\text{+}CH_2\text{)}_{\overline{m+1}}-O-A^0-R^4, \quad \text{(Ie)}$$

$$R^1-A\text{+}CH_2\text{)}_{\overline{m+1}}-OCO-A^0-R^4, \text{ and} \quad \text{(If)}$$

$$R^1-A\text{+}CH_2\text{)}_{\overline{m+1}}-COO-A^0-R^4, \quad \text{(Ig)}$$

wherein R, A, m, $A^0$ and $R^4$ have the meanings as defined above.

3. A compound according to claim 1, wherein Z is a single bond.

4. A compound according to claim 1, wherein $A^0$, $A^1$ and $A^2$ satisfy any one of the following combinations (a) to (c), or $A^0$, $A^1$, $A^2$ and $A^3$ satisfy the following combination (d), (a) $A^0$: 1,4-phenylene which is unsubstituted or substituted by at least one F, 1,4-cyclohexylene, or thiophene-2,5-diyl;

$A^1$: benzothiazole-2,6-diyl, benzoxazole-2,5-diyl, thiazole-2,5-diyl, quinoline-2,6-diyl, or quinoxaline-2,6-diyl; and $A^2$: 1,4-phenylene which is unsubstituted or substituted by at least one F;

(b) $A^0$: 1,4-phenylene which is unsubstituted or substituted by at least one F, 1,4-cyclohexylene, or thiophene-2,5-diyl;

$A^1$: indan-2,5-diyl or coumaran-2,5-diyl; and $A^2$: pyrimidine-2,5-diyl;

(c) $A^0$: 1,2-dithiolan-3,5-diyl;

$A^1$: pyrimidine-2,5-diyl or pyridine-2,5-diyl; and $A^2$: 1,4-phenylene which is unsubstituted or substituted by at least one F; and (d) A: 1,4-phenylene which is unsubstituted or substituted by at least one F, 1,4-cyclohexylene, or thiophene-2,5-diyl;

$A^1$: 1,4-phenylene which is unsubstituted or substituted by at least one F;

$A^2$: thiazole-2,5-diyl; and $A^3$: 1,4-phenylene which is unsubstituted or substituted by at least one F.

5. A compound according to claim 4, wherein Z is a single bond.

6. A compound according to claim 1, wherein $R^4$ is any one of the following groups (i) to (iv):

$$\text{n-}C_aH_{2a+1}-Y^3-, \quad \text{(i)}$$
$$C_hF_{2h+1}\text{+}CH_2\text{)}_{\overline{i}}Y^3-, \quad \text{(ii)}$$
$$F-, \text{ and} \quad \text{(iii)}$$
$$H-, \quad \text{(iv)}$$

wherein a is an integer of 1–12; i is an integer of 0–7; h is an integer of 1–9; and $Y^3$ is a single bond, —O—, —OCO— or —COO—.

7. A compound according to claim 1, wherein $R^4$ is H or F, and at least one of $Y^1$ and $Y^2$ is —$CH_2$—.

8. A compound according to claim 4, wherein $R^4$ is H or F, and at least one of $Y^1$ and $Y^2$ is —$CH_2$—.

9. A compound according to claim 1, wherein $R^1$ or $R^2$ is $R^3$, and $R^3$ is any one of the following groups (v) to (xi):

$$\text{n-}C_aH_{2a+1}-Y^3, \quad \text{(v)}$$

$$\underset{|}{CH_3} \quad \text{(vi)}$$
$$C_bH_{2b+1}CH\text{+}CH_2\text{)}_{\overline{d}}Y^3-,$$

$$\underset{|}{CH_3} \quad \text{(vii)}$$
$$C_eH_{2e+1}O\text{+}CH_2\text{)}_{\overline{f}}CH\text{+}CH_2\text{)}_{\overline{g}}Y^3-,$$

$$C_hF_{2h+1}\text{+}CH_2\text{)}_{\overline{i}}Y^3-, \quad \text{(viii)}$$

$$\underset{|}{F} \quad \text{(ix)}$$
$$C_jH_{2j+1}-CH-Y^4-,$$

$$F-, \text{ and} \quad \text{(x)}$$
$$H-, \quad \text{(xi)}$$

wherein a is an integer of 1–17; d, g and i are an integer of 0–7; b, e and h are integer of 1–9; f is 0 or 1; j is an integer of 1–16; $Y^3$ is a single bond, —O—, —OCO— or —COO—; and $Y^4$ is —$CH_2O$— or —COO—.

10. A compound according to claim 1, which is an optically active compound.

11. A compound according to claim 1, which is an optically inactive compound.

12. A liquid crystal composition comprising at least two compounds, at least one of which is a mesomorphic compound of the formula (I) according to any one of claims 1 to 11.

13. A liquid crystal composition according to claim 12, which comprises 1–80 wt. % of a mesomorphic compound of the formula (I).

14. A liquid crystal composition according to claim 12, which comprises 1–60 wt. % of a mesomorphic compound of the formula (I).

15. A liquid crystal composition according to claim 12, which comprises 1–40 wt. % of a mesomorphic compound of the formula (I).

16. A liquid crystal composition according to claim 12, which has a chiral smectic phase.

17. A liquid crystal device, comprising a pair of substrates and a liquid crystal composition according to claim 12 disposed between the substrates.

18. A device according to claim 17, which further comprises an alignment control layer.

19. A device according to claim 18, wherein the alignment control layer has been subjected to uniaxial alignment treatment.

20. A device according to claim 17, wherein the liquid crystal composition is disposed in a thickness suppressing formation of a helical structure of liquid crystal molecules between the substrates.

21. A liquid crystal apparatus comprising a liquid crystal device according to claim 17.

22. An apparatus according to claim 21, wherein the liquid crystal device is used as a display device.

23. An apparatus according to claim 21, which further comprises a drive circuit for the liquid crystal device.

24. An apparatus according to claim 22, which further comprises a light source.

25. A display method, comprising:

providing a liquid crystal composition according to claim 12; and controlling the alignment direction of liquid crystal molecules to effect display.

* * * * *

UNITED STATES PATENT AND TRADEMARK OFFICE
CERTIFICATE OF CORRECTION

PATENT NO.    : 5,462,694
DATED         : October 31, 1995
INVENTOR(S)   : Yoko Kosaka et al.

It is certified that error appears in the above-identified patent and that said Letters Patent is hereby corrected as shown below:

Title page,
Item [56], References Cited, FOREIGN PATENT DOCUMENTS,
"4258684" should read -- 4-258684 --.
"4264192" should read -- 4-264192 --.

Column 2,
Line 30, "electric" should read -- electric field --.

Column 3,
Line 41, "tile" should read -- tilt --.

Column 4,
Line 1, "an" should read -- a --.
Line 22, "$R^1$-$A^{R2}$      (I)," should read -- $R^1$A-$R^2$      (I), --.

Column 7,
Line 36, "are integer" should read -- are an integer --.

Column 8,
Line 15, "?" should be deleted.
Line 16, "?" should be deleted.
Line 17, "?" should be deleted.
Line 18, "$A^0Y^1$," should read -- $A^0$, $Y^1$, --.

Column 12,
Line 23, "$C_{12}H_{25}O$" should read -- $C_{12}H_{25}$ --.

Column 13,
Line 56, "$C_8H_7$" should read -- $C_8H_{17}$ --.

Column 15,
Line 51, " 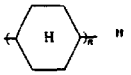 " should read -- 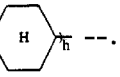 --.

Column 20,
Line 27, "$\underline{C}$" should read -- $C$ --.
Line 31, "C" should read -- $C$ --.

UNITED STATES PATENT AND TRADEMARK OFFICE
CERTIFICATE OF CORRECTION

PATENT NO.   : 5,462,694
DATED        : October 31, 1995
INVENTOR(S)  : Yoko Kosaka et al.

It is certified that error appears in the above-identified patent and that said Letters Patent is hereby corrected as shown below:

Column 24,
Line 64, "follwoing" should read -- following --.

Column 26,
Line 27, "$\underline{2}$" should read -- 2 --.
Line 30, "C" should read -- $C$ --.

Column 28,
Line 31, "and" should read -- to --.

Column 30,
Line 66, "formula" should read -- formulas --.

Column 32,
Line 46, "C" should read -- $C$ --.

Column 33,
Line 22, "$R_6^1$" should read -- $R_8^1$ --.
Line 26, "$R_6^1$" should read -- $R_8^1$ --.

Column 34,
Line 47, "$\underline{C}$" should read -- $C$ --.
Line 50, "C" should read -- $C$ --.

Column 36,
Line 42, "oh" should read -- on --.

Column 37,
Line 24, "with," should read -- with --.

Column 40,
Line 64, "an" should read -- any --.

Column 44,
Line 66, "second" should read -- seconds --.

UNITED STATES PATENT AND TRADEMARK OFFICE
CERTIFICATE OF CORRECTION

PATENT NO.   : 5,462,694
DATED        : October 31, 1995
INVENTOR(S)  : Yoko Kosaka et al.

It is certified that error appears in the above-identified patent and that said Letters Patent is hereby corrected as shown below:

Column 50,
Line 1, "devices were" should read -- device was --.
Line 62, "-$CH_2$-," should read -- -$CH_2O$-, --.

Column 51,
Line 27, "R," should read -- $R^1$, --.
Line 54, "(d)  A:" should read -- (d)  $A^0$: --.

Column 52,
Line 34, "are integer" should read -- are an integer --.

Signed and Sealed this

Twenty-third Day of July, 2002

*Attest:*

*Attesting Officer*

JAMES E. ROGAN
*Director of the United States Patent and Trademark Office*